(12) United States Patent
Hoffmann et al.

(10) Patent No.: US 8,855,389 B1
(45) Date of Patent: Oct. 7, 2014

(54) AUTOMATED PATIENT-SPECIFIC BONE-IMPLANT BIOMECHANICAL ANALYSIS

(71) Applicant: O.N.Diagnostics, LLC, Berkeley, CA (US)

(72) Inventors: Paul Frederick Hoffmann, Oakland, CA (US); Tony M. Keaveny, Berkeley, CA (US); David L. Kopperdahl, Berkeley, CA (US)

(73) Assignee: O.N.Diagnostics, LLC, Berkeley, CA (US)

( * ) Notice: Subject to any disclaimer, the term of this patent is extended or adjusted under 35 U.S.C. 154(b) by 0 days.

(21) Appl. No.: 14/150,631

(22) Filed: Jan. 8, 2014

Related U.S. Application Data

(63) Continuation of application No. 13/401,585, filed on Feb. 21, 2012, now Pat. No. 8,644,568, which is a continuation-in-part of application No. 12/510,225, filed on Jul. 27, 2009, now Pat. No. 8,126,234.

(60) Provisional application No. 61/083,875, filed on Jul. 25, 2008.

(51) Int. Cl.
*G06K 9/00* (2006.01)
*G06T 7/00* (2006.01)
*A61B 6/03* (2006.01)
*A61B 5/00* (2006.01)

(52) U.S. Cl.
CPC ............ *A61B 5/4851* (2013.01); *G06T 7/0012* (2013.01); *A61B 6/032* (2013.01)
USPC ............................ 382/128; 600/420; 606/151

(58) Field of Classification Search
USPC ................. 382/100, 128, 129, 130, 131, 132; 128/922; 378/4–27; 600/420, 421; 606/151, 285; 623/22.33, 23.54
See application file for complete search history.

(56) References Cited

U.S. PATENT DOCUMENTS

| 5,172,695 | A | | 12/1992 | Cann et al. | |
| 5,769,092 | A | * | 6/1998 | Williamson, Jr. .............. | 128/898 |
| 6,266,453 | B1 | * | 7/2001 | Hibbard et al. ................ | 382/294 |
| 6,629,997 | B2 | * | 10/2003 | Mansmann ................ | 623/14.12 |
| 6,712,851 | B1 | * | 3/2004 | Lemperle et al. .......... | 623/16.11 |
| 7,124,067 | B2 | * | 10/2006 | Ascenzi .......................... | 703/11 |
| 7,134,874 | B2 | | 11/2006 | Chishti et al. | |
| 7,353,153 | B2 | * | 4/2008 | Ascenzi et al. ................. | 703/11 |
| 7,427,200 | B2 | * | 9/2008 | Noble et al. .................. | 434/274 |
| 7,542,791 | B2 | | 6/2009 | Mire et al. | |

(Continued)

OTHER PUBLICATIONS

Bessho, M., et al., Prediction of strength and strain of the proximal femur by a CT-based finite element method. Journal of Biomechanics, 2007. 40(8): p. 1745-53.

(Continued)

*Primary Examiner* — Anand Bhatnagar
(74) *Attorney, Agent, or Firm* — Patent Law Offices of Michael E. Woods; Michael E. Woods

(57) ABSTRACT

An apparatus, method, and computer program product for providing information for surgical planning based on automated biomechanical analysis of a bone-implant system using finite element analysis of a patient's 3D medical image, including automated biomechanical analysis of bone-implant systems for use in surgical planning both pre-operatively and intra-operatively and for use in research and development studies.

12 Claims, 12 Drawing Sheets

(56) References Cited

U.S. PATENT DOCUMENTS

| | | | |
|---|---|---|---|
| 7,550,008 B2 * | 6/2009 | Ralph et al. | 623/17.11 |
| 7,824,433 B2 * | 11/2010 | Williams | 606/285 |
| 7,837,621 B2 * | 11/2010 | Krause et al. | 600/300 |
| 8,126,234 B1 | 2/2012 | Edwards et al. | |
| 8,331,634 B2 * | 12/2012 | Barth et al. | 382/128 |
| 8,532,361 B2 * | 9/2013 | Pavlovskaia et al. | 382/131 |

OTHER PUBLICATIONS

Chao, C.K., et al., Increasing bending strength and pullout strength in conical pedicle screws: biomechanical tests and finite element analyses. J Spinal Disord Tech, 2008. 21(2): p. 130-8.

Chen, W.P., et al., Selection of fixation devices in proximal femur rotational osteotomy: clinical complications and finite element analysis. Clin Biomech (Bristol, Avon), 2004. 19(3): p. 255-62.

Chen, C.S., et al., Failure analysis of broken pedicle screws on spinal instrumentation. Medical Engineering and Physics, 2005. 27(6): p. 487-96.

Couteau, B., Y. Payan, and S. Lavallée, The mesh-matching algorithm: an automatic 3D mesh generator for finite element structures. Journal of Biomechanics, 2000. 33(8): p. 1005-9.

Estok, D.M., 2nd, T.E. Orr, and W.H. Harris, Factors affecting cement strains near the tip of a cemented femoral component. J Arthroplasty, 1997. 12(1): p. 40-8.

Gao, J., W. Xu, and Z. Ding, 3D finite element mesh generation of complicated tooth model based on CT slices. Comput Methods Programs Biomed, 2006. 82(2):p. 97-105.

Grauer, J.N., et al., Biomechanics of two-level Charite artificial disc placement in comparison to fusion plus single-level disc placement combination. The Spine Journal, 2006. 6(6): p. 659-666.

Helwig, P., et al., Finite element analysis of a bone-implant system with the proximal femur nail. Technol Health Care, 2006. 14(4-5): p. 411-9.

Keyak, J. H., et al., Prediction of femoral fracture load using automated finite element modeling. J Biomech, 1998. 31 (2): p. 125-33.

Kluess, D., et al., A convenient approach for finite-element-analyses of orthopaedic implants in bone contact: modeling and experimental validation. Comput Methods Programs Biomed, 2009. 95(1): p. 23-30.

Kwon, G.-H., S.-W. Chae, and K.-J. Lee, Automatic generation of tetrahedral meshes from medical images. Computers & Structures, 2003. 81(8-11): p. 765-775.

Lee, K.K., et al., Finite-element analysis for lumbar interbody fusion under axial loading. IEEE Trans Biomed Eng, 2004. 51(3): p. 393-400.

Prendergast, P.J., Finite element models in tissue mechanics and orthopaedic implant design. Clin Biomech (Bristol, Avon), 1997. 12(6): p. 343-366.

Reggiani, B., et al., Predicting the subject-specific primary stability of cementless implants during pre-operative planning: preliminary validation of subject-specific finite-element models. J Biomech, 2007. 40(11): p. 2552-8.

Sowmianarayanan, S., A. Chandrasekaran, and R.K. Kumar, Finite element analysis of a subtrochanteric fractured femur with dynamic hip screw, dynamic condylar screw, and proximal femur nail implants—a comparative study. Proc Inst Mech Eng H, 2008. 222(1): p. 117-27.

Sullivan, J.M., G. Charron, and K.D. Paulsen, A three-dimensional mesh generator for arbitrary multiple material domains. Finite Elements in Analysis and Design, 1997. 25(3-4): p. 219-241.

Tai, C.L., et al., Finite element analysis of the cervico-trochanteric stemless femoral prosthesis. Clin Biomech (Bristol, Avon), 2003. 18(6): p. S53-8.

Teo, J.C., et al., Heterogeneous meshing and biomechanical modeling of human spine. Medical Engineering and Physics, 2007. 29(2): p. 277-90.

Viceconti, M., et al., Automatic generation of accurate subject-specific bone finite element models to be used in clinical studies. Journal of biomechanics, 2004.37(10): p. 1597-605.

Viceconti, M., et al., Primary stability of an anatomical cementless hip stem: a statistical analysis. J Biomech, 2006. 39 (7): p. 1169-79.

Waide, V., et al., Modelling the fibrous tissue layer in cemented hip replacements: experimental and finite element methods. J Biomech, 2004. 37(1): p. 13-26.

Wang, Z.L., et al., Computational biomechanical modelling of the lumbar spine using marching-cubes surface smoothened finite element voxel meshing. Comput Methods Programs Biomed, 2005. 80(1): p. 25-35.

* cited by examiner

AUTOMATED PATIENT-SPECIFIC BONE-IMPLANT BIOMECHANICAL ANALYSIS

CROSS REFERENCE TO RELATED APPLICATIONS

This application is a Continuation of U.S. application Ser. No. 13/401,585 filed 21 Feb. 2012 which was a Continuation-In-Part of U.S. application Ser. No. 12/510,225, filed 27 Jul. 2009 which claims the benefit of U.S. Provisional Application No. 61/083,875, filed Jul. 25, 2008, entitled AUTOMATED PATIENT-SPECIFIC BONE-IMPLANT BIOMECHANICAL ANALYSIS, the disclosures of which are herein incorporated by reference in their entireties for all purposes.

BACKGROUND OF THE INVENTION

The present invention relates generally to a method and system for orthopaedic surgical planning and more specifically to surgical planning based on an automated finite element analysis of a bone-implant system using a 3D medical image of a patient.

Orthopaedic implants and the bone they are implanted into often must endure large stresses from habitual and sporadic loading and consequently the implants sometimes fail or loosen. Biomechanical analysis of a bone-implant system is often performed as part of the design process for such implants and it has been proposed that patient-specific biomechanical analysis of bone-implant systems could be used clinically to improve surgical planning. The information derived from such analyses could aid the surgeon in choosing an optimal size and position of a given implant design for a particular patient, or even choose among different implant designs. With more elderly individuals undergoing various orthopaedic and spine surgical procedures, there is also a need to assess a structural integrity of the underlying bone since it is possible that proposed bone is too weak to sustain the stresses that develop around the implant which could result in a loosening of the implant. Identifying patients having structurally insufficient bone as part of the surgical planning process enables surgeons to plan accordingly in the care of such patients, perhaps using a different size implant, an implant of a different design, augmenting the fixation of the implant using bone cement, biologics, or some other means, putting the patient on a bone-strengthening drug treatment, or even foregoing surgery.

Finite element modeling of a bone-implant system, based on the medical image of the patient (patient-specific), can be used for such purposes. While a number of references in the field have applied such finite element modeling techniques in research studies, for clinical implementation, a challenge is to automate this analysis to such a degree so that the analysis is available to a surgeon, radiologist, radiological imaging technician, or such other medical professional who has no technical expertise in finite element modeling. Further, the technique should be capable of being executed rapidly so that it can be performed intra-operatively or as the surgeon reviews the medical image; and the technique should be applicable to any bone geometry, shape, or size so that it can be applied confidently to any patient. There are no such techniques in the field for patient-specific modeling of bone-implant systems that meet all these criteria. Indeed, regarding clinical implementation of such patient-specific bone-implant finite element analyses, Helwig et al. recently reported that such analyses "are not yet possible in daily routine as an automatic algorithm for biomechanical assessment does not exist" (Helwig P, Faust G, Hindenlang U, Kroplin B, and Eingartnew C, Technology and Health Care 14: 411-419, 2006).

Patient-specific finite element models of orthopaedic bone-implant systems can be created from 3D CT scans. See for example, Keaveny T M and Bartel D L, Journal of Bone and Joint Surgery [Am], 77-A:911-923, 1995; Chen Si, Lin R M, Chang C H, Medical Engineering & Physics, 25:275-282, 2003; Waide V, Cristofolini L, Stolk J, Verdonschot N, Boogaard G J, and Toni A, Journal of Biomechanics 37: 13-26, 2004. The general approach in these types of patient-specific finite element analyses has been to create a finite element mesh of the implant, and then build around that a compatible finite element mesh of the endosteal or periosteal surface of the bone. Each new bone to be analyzed requires a new finite element mesh of the bone to be constructed about the finite element mesh of the implant. Since this is a tedious process, this technique has never been applied to more than a few bones in a research setting. One problem with this approach is that it is difficult to automate in a clinical setting due to the great degree of population variability in the geometry of the bones of patients. This variability often requires an expert user to adjust the finite element mesh for the bone in order to avoid highly distorted finite elements, which are problematic numerically in the subsequent finite element analysis. Thus, while various methods for creation of such bone-implant meshes may work for regularly-sized and shaped bones, these algorithms typically require expert user input to deal with distorted elements in cases where the bone geometry is unusual or the implant geometry is complex. These techniques can therefore not be applied to large numbers of patients in an automated manner in near real-time by persons unskilled in finite element analysis.

Many of the same limitations are applicable to finite element meshes that are autopaved (i.e. automatically filled with 2D or 3D finite elements), either using tetrahedral, hexahedral, or some other type of finite element or a combination thereof. While automatic tetrahedral mesh generators can model the curvature of whole bones (see for example: G H Kwon, S W Chae, K J Lee, Computer and Structures 81:765-775, 2003; Viceconti M, Davinelli M, Taddei F, and Cappello A, Journal of Biomechanics 37: 1597-1605, 2004), the number of elements to do so in the presence of an implant would typically result in prohibitively large models that would be computationally very expensive to solve in a clinical context, particularly when one is to capture such implant detail as screw threads in the finite element mesh and small gaps between the implant and bone. For example, Tai et al. used automatic paving with 10-noded tetrahedral elements in a model of a proximal femur with stemless prosthesis. They reported that "the threads and the tips of the fixation screws were not modeled in the FEM in order to simplify the model setup" (Tai C L, Shih C H, Chen W P, Lee S S, Kiu Y L, Hsieh P H, and Chen W J, Clinical Biomechanics 18:S53-S58, 2003.) Even so, they needed more than 20,000 10-noded tetrahedral elements and had to solve the resulting analysis on a supercomputer.

When using such autopaving, mesh distortion can also occur around the edges of some bones, particularly in regions of degenerative changes where the bone geometry becomes very irregular. Mesh distortion is also an issue for use with deformable registration techniques, in which a "master" mesh of bone-implant system is "deformed" mathematically to fit the geometry of a digital image of a bone. For example, Couteau et al. reported that about 15% of the elements in their deformable registration-based meshing technique were distorted, according to standard measures of element distortion (Couteau B, Payan Y, and Lavallee S, Journal of Biomechanics 33: 1005-1009, 2000). None of the 10 cadaver femurs in that study showed any signs of pathology and there were no implants modeled. In a clinical situation, for certain patients with unusual bone geometries due to various types of pathology, highly distorted elements will inevitably result from such an automated meshing technique—especially when applied to a bone-implant situation. As a result of these limitations, none of these prior art techniques have found any clinical use for bone-implant surgical planning purposes and there are no commercial applications of any such techniques that are suitable for clinical use.

One particular type of autopaving technique that has been used in research studies for analysis of orthopaedic bone-implant systems is the "voxel-based" technique, in which every finite element in the mesh is cube-shaped and derived directly from the underlying CT image. However, this voxel-based approach provides a poor description of the surface of the implant because the geometry of the implant surface is forced to conform with the cube shape of the voxels. Thus, this approach does not work well for curved implants, flat implants that are placed oblique to the coordinate system of the cube-shaped voxels, or any implants that contain complex non-voxel geometric features such as screw threads, fenestrations, holes, filets and the like. Since maximum stresses in the implant typically occur on its surface and around such complex features, and since bone-implant interface stresses are key to assessing implant loosening, the use of such voxel-based meshes at the bone-implant interface is not desirable. Described originally in the early 1990's (see, for example, Skinner H B, Kim A S, Keyak J H, Mote C D: "Femoral prosthesis implantation induces changes in bone stress that depend on the extent of porous coating." Journal of Orthopaedic Research 12:553-563, 1994), the voxel-based technique has not since been modified for improved performance and has not found any clinical usage.

As a result of the above limitations with the currently available technology, there remains a need for a simple, general method that accurately models the bone-implant interface and surrounding tissue and that in application can be applied rapidly and in a fully automated fashion in a clinical setting such that it can be used reliably for any patient without the need for any technical expertise in finite element modeling or mesh creation. The technique should also be applicable to many different types of implants and to situations when more than one implant is placed in the same bone, such as a plate with screws.

One additional issue that challenges full automation for clinical usage is the initial positioning and sizing of the implant within the bone. Given the complex 3D nature of most bones, and the heterogeneity in bone density both with any bone from a given patient and across different patients, it is oftentimes difficult to properly size and position a given implant design for a given patient, and in some cases it is even difficult to choose between different implant designs for a given patient since some implants might work better in certain patients but worse in others due to the complex bone-implant load-transfer characteristics associated with the 3D nature of the bone geometry and the spatially varying distribution of bone density. While techniques exist for image-based surgical planning and implant placement from medical images (see for example, U.S. Pat. Nos. 7,542,791 and 7,134,874), it would be desirable to have a technique that helps optimize the sizing and positioning of an implant for a given patient based on a finite element analysis of the implant in that patient—and to do so in an automated, cost-effective manner that would be feasible clinically both as pre-operative surgical planning and intra-operatively. Automation is crucial when the system is to be used by the surgeon, speed is critical when the system is to be used intra-operatively, and generality is required when the technique is to be applicable to any patient.

BRIEF SUMMARY OF THE INVENTION

A system and method is presented for automated finite element analysis of bone-implant systems for use in surgical planning both pre-operatively and intra-operatively; the technique can also be used in research and development studies and for design of implants. Use of the system and application of the method require no knowledge of finite element meshing techniques and thus can be applied reliably to any patient by a surgeon or technician having no training in finite element modeling.

A preferred method includes four general steps in which: 1) a digital medical image of a bone or portion thereof is received; 2) a specific implant is chosen and digitally positioned within the medical image; 3) a pre-constructed non-patient-specific bone implant finite element mesh, taken from a library of such pre-constructed meshes, is converted into a patient-specific bone implant finite element model; and 4) a finite element analysis is performed and results made available. The pre-constructed non-patient-specific bone implant finite element mesh is usable on any patient and in a fully automated fashion. Thus, embodiments of this invention eliminate any need for a user to have to adjust a patient-specific finite element mesh of the bone-implant system, and thus facilitates the application of this technique to analysis of any patient, regardless of their bone geometry or density.

In the first step, a digital medical image of the patient's bone or portion thereof is received. Typically, for a three-dimensional analysis, this image would comprise a CT scan, but MRI images may be suitable in certain circumstances or other medical images from which a bone-implant model can be created. For two-dimensional analyses, a DXA scan or digital X-ray could be used, for example.

In the second step, computerized techniques are used to position a digital model of a specified implant, obtained from a library of such digital models actually available for the surgical procedure, within a processed version of the digital medical image in which the bone of interest or portion thereof is appropriately oriented and segmented. Such computerized techniques may include deformable registration, as described here in a preferred embodiment, or, more traditional image processing techniques that might involve interaction with a user for virtual positioning of the implant within the bone.

In the third step, a pre-constructed non-patient-specific bone implant finite element mesh, taken from a library of such pre-constructed non-patient-specific bone-implant meshes, is digitally registered to, and superimposed on, the medical image of the first step using the positional information obtained from the second step. This pre-constructed non-patient-specific bone-implant mesh comprises a detailed finite element mesh of the implant, connected to a more general finite element mesh of all surrounding material. In the preferred embodiment, the envelope of this pre-constructed bone-implant mesh extends beyond the periosteal surface of the entire bone, thus including any biological tissue or air or gaps immediately adjacent to the implant, the bone itself, and any material (soft tissue, air, blood vessels and so forth) beyond the periosteal surface of the bone but within the envelope of the non-patient-specific bone-implant mesh. This mesh is then masked using the information in the segmented medical image to provide a patient-specific external geometry for the mesh. This masking removes all elements outside the periosteal surface of the bone but otherwise does not alter the geometry of any individual finite elements in the model, thereby avoiding any distortion of elements. Using gray scale information in the medical image, patient-specific material properties are then assigned to all elements in this masked finite element mesh except for those elements representing the implant and the bone-implant interface conditions, all of which have pre-defined constitutive properties.

In the fourth step, after applying pre-defined boundary conditions to the now patient-specific finite element mesh, a finite element analysis is performed to measure biomechanical characteristics of the bone-implant system for the patient. The result of this analysis is then saved in computer memory; it can be printed in a medical report that can be used by surgeons for surgical planning purposes; it can be output to digital data files for use by engineers for implant design purposes; or it can be displayed on a computer terminal for intra-operative use by the surgeon or other medical professionals, among other uses.

An important aspect of the present invention is within the third step, by way of its use of a library of pre-constructed non-patient-specific bone-implant meshes, and its combination of this step with the other three steps. As a result, a detailed finite element mesh of the implant, a surface of the implant, the bone-implant interface, and any neighboring tissue are automatically created for any patient, regardless of the complexity of the morphology of their bone. Addressing some major limitations of conventional systems, distorted elements never occur because the entire bone-implant mesh is previously constructed without any distorted elements. The periosteal geometry of the bone is patient-specific because it is defined by masking of the medical image; when the finite elements in the non-patient-specific bone-implant mesh are small, any discretization error in defining the external geometry of the bone by such masking of the pre-constructed finite element mesh should be small. The material properties assigned in the model to the material immediately adjacent to the implant surface are patient-specific because they are defined by the gray scale information contained within the digital medical image of the specific bone designated for implant. The technique is preferably fully automated for use in a clinical setting since the non-patient-specific bone-implant finite element mesh is taken from a library of such pre-constructed meshes, and beyond masking, which is a standard image processing task that can be highly automated, no other adjustments need to be made to the finite element mesh in order to customize its geometry for any given patient. Thus, a user never needs to intervene to adjust the finite element mesh during application of this method in a clinical setting.

In the above preferred embodiment, the envelope of the pre-constructed non-patient-specific bone-implant mesh extends beyond the periosteal surface of the bone. In a second preferred embodiment, the envelope of the pre-constructed non-patient-specific bone-implant mesh extends beyond the implant surface into the bone but not necessarily beyond the periosteal surface of the bone, and autopaving is used to extend the mesh of the bone to the periosteal surface of the bone. In this case, the pre-constructed non-patient-specific bone-implant mesh contains the implant, the bone-implant interface, and some of the surrounding material about the implant (bone, marrow, soft tissue, gaps, air, fluid, and the like). Further, the external envelope of the pre-constructed non-patient-specific bone-implant mesh in this case always extends beyond the surface of the implant and has a geometrically regular geometry; it also has a surface node distribution that facilitates autopaved meshing from its external surface to the periosteal surface of the bone. Such autopaving could consist of a purely voxel mesh, a purely tetrahedral mesh, or any combination of element types. A number of techniques for such autopaved meshing could be used for such purposes. In addition, instead of autopaving to the periosteal surface of bone, in some applications it may be desired to autopave instead to the endosteal surface of the bone, the inner surface of the cortical bone, or some other internal bone surface.

Because the pre-constructed non-patient-specific bone-implant mesh is chosen from a library of pre-constructed meshes, the technique can be applied in a fully automated fashion to a bone of any size or shape. For the same reason, the technique can also be applied to many clinical situations, e.g. artificial hip and knee implants, pedicle screws, fracture fixation plates and pins, various types of screws, and the various forms of inter-vertebral spinal fusion devices. Separate libraries of pre-constructed non-patient-specific bone-implant meshes would be created for each of these clinical applications, and for each different design of implant within any specific clinical application. Conceptually, embodiments of this invention moves the effort of mesh generation up front and out of the clinic, such that the pre-constructed non-patient-specific bone-implant mesh is created a priori—perhaps manually—for a given implant design. Once that non-patient-specific bone-implant mesh is constructed, it may then be applied in clinical applications to any patient in an automated fashion.

This pre-constructed non-patient-specific bone-implant meshing technique overcomes the limitations of autopaving using a fully voxel mesh because it is adaptable to include any desired level of mesh fidelity for the implant surface and at the bone-implant interface; it overcomes the limitations of full tetrahedral paving because it requires far fewer elements and eliminates any possibility of element distortion particularly around the implant surface and in any regions where the distance between the bone external surface the implant surface is small; it overcomes the limitations of a deformable registration-based meshing technique because it eliminates any possibility of element distortion. The superior degree of generality and automation offered by the pre-constructed non-patient-specific bone-implant meshing technique over the prior art is clinically important because surgeons will not use any finite element-based surgical planning technique unless it can be applied by the surgeon to any patient in a reliable manner without the need for the surgeon to have any technical expertise in finite element modeling.

An important application, made clinically feasible by the highly automated nature of the disclosed method, is the use of a panel of virtual stress testing studies in a clinical setting for the purposes of surgical planning, wherein a number of pre-defined-different surgical options are analyzed by altering the patient-specific finite element model in a variety of ways. Specifically, a panel of studies is automatically performed in which a variety of different pre-constructed non-patient-specific bone-implant meshes, all taken from the library of such pre-constructed meshes, are sequentially used for the same patient by repeating the above steps. In one specific application, the position and size of the implant can be optimized by perturbing the size and position of the implant within the bone in the first step and finding the configuration that provides optimal biomechanical outcomes. In another application, different implant designs can be tested by specifying a different implant in the first step. In another application, the response of the bone-implant system to hypothetical changes in bone characteristics over time—in response to various therapeutic agents or to the effects of aging or disease—can be simulated by altering how the bone material properties are assigned in the third step. Prior knowledge of probable temporal changes in bone material properties can be used to customize the probable temporal bone changes to the specific patient under analysis. A statistical atlas of such changes can be used for such purposes. All such studies are made clinically feasible by the use of the pre-constructed non-patient-specific bone-implant meshing technique.

The method is versatile since it also enables automated finite element modeling of applications in which more than one implant is used in the same bone, such as a plate with multiple screws attached to a long bone, or two pedicle screws attached to a vertebra. Examples of these applications are described below.

In another embodiment, particularly useful for use with two or more implants, a chosen pre-constructed non-patient-specific bone-implant mesh can be further modified using deformable meshing techniques. This can facilitate use with multiple implants that are in contact with each other and attached to the same bone but which have variable relative positions with respect to each other due to patient characteristics such as bone geometry and density. This deformable meshing can be used during clinical application and can also be used to increase the number of variations of a given pre-constructed non-patient-specific bone-implant mesh in the library for future use. In this embodiment, a pre-constructed non-patient-specific bone-implant mesh is chosen from the library that corresponds most closely, but not exactly, to a prescribed position of the two or more implants in the patient's bone. The pre-constructed non-patient-specific bone-implant mesh contains the two or more implants and the surrounding material. The portions of the mesh defining the two implants are then rigidly moved with respect to each other in order to better match the prescribed configuration and the remaining mesh elements are smoothly deformed; this transformation is only allowed up to the point that it does not result in any element distortion in the altered pre-constructed non-patient-specific bone-implant mesh. The improved position of the implants relative to each other is then used in the finite element analysis during clinical application. The resulting altered non-patient-specific bone-implant mesh can also be added to the digital library of non-patient-specific bone-implant meshes for future use as a pre-constructed non-patient-specific bone implant mesh. This process can be applied during clinical application or in advance, with the purpose of increasing the number of variations of any given pre-constructed non-patient-specific bone implant mesh in the library.

DETAILED DESCRIPTION OF THE INVENTION

The present invention relates to surgical planning using a fully automated method of finite element modeling of bone-implant systems. The present invention may be used in a variety of clinical surgical planning applications, including but not limited to hip, spine, or knee surgery, total joint replacement, spinal fusion, pedicle screw fixation, and fracture fixation. While applicable to any clinical imaging modality—MRI, DXA, or X-rays—and to any bone-implant system, the technique is described in detail below for use with CT scans. In the following description, numerous specific details are set forth in order to provide a thorough understanding of the present invention. It will be apparent, however, to one skilled in the art, that the present invention may be practiced without some or all of these specified details and may be applied to any medical imaging modality and to any bone-implant system in which a goal is to perform a biomechanical analysis of such bone-implant system. In some instances, well known process steps of biomechanical analysis, finite element modeling, computer vision-based image processing, and more traditional image processing have not been described in detail in order to not unnecessarily obscure the present invention.

The following detailed descriptions are presented to enable one of ordinary skill in the art to make and use the invention and are provided in the context of a patent application and its requirements. Various modifications to the preferred embodiment and the non-patient-specific principles and features described herein will be readily apparent to those skilled in the art. Thus, the present invention is not intended to be limited to the embodiments shown but is to be accorded the widest scope consistent with the principles and features described herein.

Figure 1:
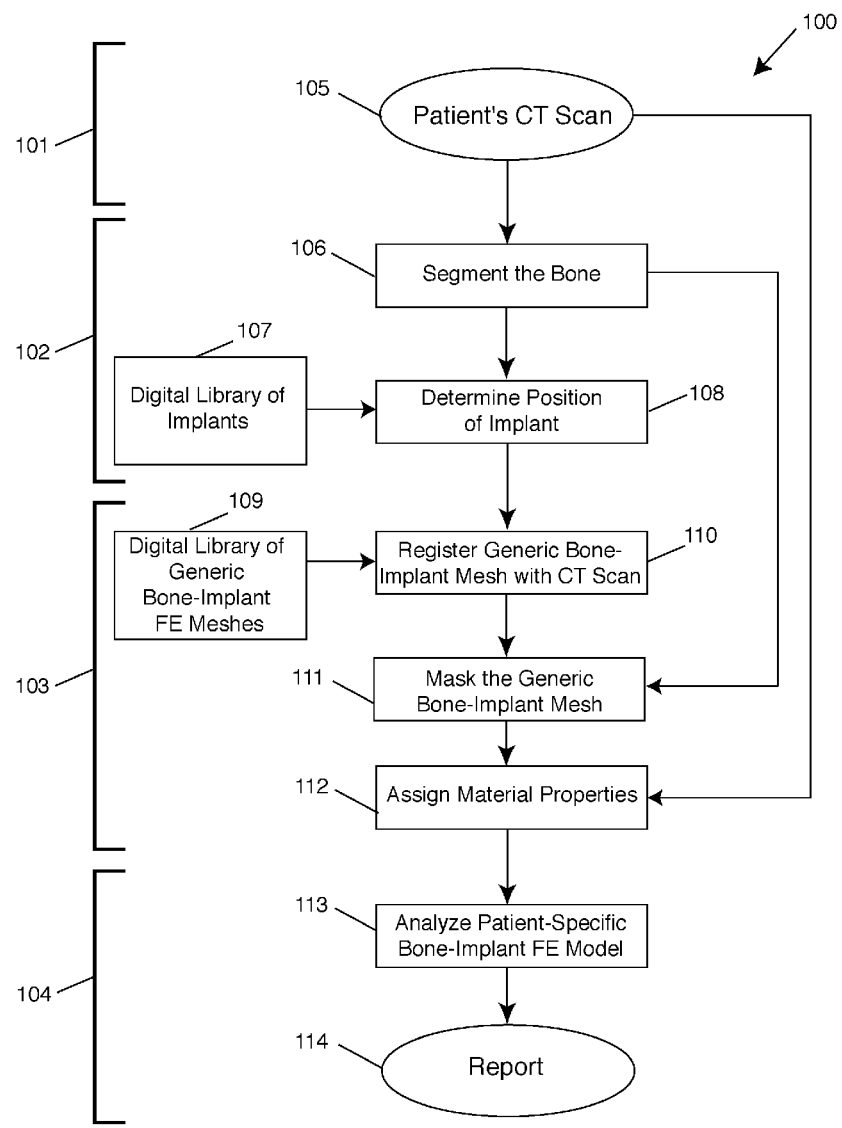
FIG. 1 is a flowchart of a preferred embodiment of the method, primarily based on masking of a pre-constructed non-patient-specific bone-implant mesh.

FIG. 1 is a flow chart of method 100 of the automated patient-specific bone-implant finite element analysis. Method 100 takes a clinical CT scan of a bone 105 and produces an output medical report 114 or a digital data file or else stores data in computer memory and displays results on a computer terminal. The four steps to the system—steps 101, 102, 103, and 104 as shown in FIG. 1—are described next in detail.

In first step 101, a digital CT scan is received by a computer. The CT scan contains the bone of interest and perhaps other bones and organs. CT images could be generated by a traditional CT scanner, or, by portable or intra-operative C-Arm or O-Arm types of CT scanners. Typically, the CT scan is stored and transferred between computers in DICOM format. While CT images are typically most useful for biomechanical analysis of bone-implant systems, MRI, DXA or other images may also be used.

Second step 102 masks the bone of interest and virtually positions the implant within the bone of interest of a particular patient. In process 106, the bone of interest is identified and segmented to separate it from any surrounding tissue in the CT scan. The segmentation is represented in software as a mask, which is stored for later use. It should be understood by one of ordinary skill in the art of medical image processing that various image-processing techniques can be used for segmentation. After segmentation, the bone mask is created and stored for later use. The bone mask is a 3D closed surface defining the outer boundary of the bone structure of interest. It represents that portion of the CT image to be included in the patient-specific bone-implant mesh. Standard techniques exist in the art to define such a closed surface in software. For example, one such method is a polygonal mesh, defined by a set of vertices joined by 2D faces; another method is a binary (0/1) image, in which a 1 may denote voxels inside the bone and a 0 those outside. It should be understood by one of ordinary skill in the art of medical image processing that various image-processing techniques can be used for segmentation and subsequent creation of the mask.

Next, the type of implant to be analyzed is chosen from a pre-constructed digital library 107 of implant images. These images may contain all the geometric features of the implant, or, may contain only that information necessary for implant positioning. Design features not critical to implant placement, such as screw thread design on a pedicle screw, may be omitted from the digital image of the implant for the purposes of positioning the implant. For a pedicle screw, for example, such a simplified image might be represented as a straight cylinder of constant diameter without threads in which different sizes of such a generalized implant would be specified by its diameter and length. In process 108, the digital image of the implant is virtually placed within the digital image of the patient's bone in order to determine the position of the implant within the bone. This virtual placement can be done with user interaction via a number of methods. A digital image of the pre-constructed bone-implant finite element mesh could also be used for such purposes since it contains all information regarding the geometry of the implant.

A variety of methods of medical image processing can be used for step 102. To better automate step 102 for more convenient clinical implementation, one could use instead a deformable registration technique for this image processing, described later in an alternative embodiment.

The purpose of third step 103 is to convert a pre-constructed non-patient-specific bone-implant finite element mesh into a patient-specific bone-implant finite element mesh. By "non-patient-specific", it is meant that the finite element mesh is not specific to the patient being analyzed; the pre-constructed non-patient-specific finite element mesh could therefore be used for analysis of any patient. Herein lies an important contribution of embodiments of the present invention. The pre-constructed non-patient-specific bone-implant finite element mesh, corresponding to the specific implant chosen in step 102 for analysis, is selected from digital library 109 of such pre-constructed non-patient-specific bone-implant finite element meshes. For a specified implant design, there will be a variety of pre-constructed non-patient-specific finite element meshes representing the different specific variations of that implant design. For example, for a given design of a pedicle screw, there are a variety of different versions of the same design, typically specified by a diameter measurement and length measurement. Digital library 109 contains a pre-constructed non-patient-specific bone-implant finite element mesh for each design option of the pedicle screw, and one of these design options would be selected for analysis. Such variations in implant design options might also include features associated with different surface finishes. That information would be contained in the pre-constructed finite element mesh by using different assumed properties of the bone-implant interface, such as a variable coefficient of friction or variable interface tensile strength. The pre-constructed non-patient-specific bone-implant finite element mesh can be tagged with all such material property and interface constitutive information associated with the design of the specific implant under analysis.

The pre-constructed non-patient-specific bone-implant meshes of the preferred embodiments always include finite elements for at least some of the surrounding bone, and in this preferred embodiment, the pre-constructed non-patient-specific bone-implant finite element mesh extends beyond the periosteal surface of the bone; or widespread application, it would be convenient to have this mesh extend substantially beyond the size of any typical bone under analysis so it would always extend beyond the periosteal surface of any specific patient being analyzed.

Inclusion of such surrounding material serves two purposes. First, it provides a detailed finite element mesh of any material (bone, gap, marrow, or soft tissue) adjacent to the implant, which is important for patient-specific material property assignment to the surrounding material. When the pre-constructed non-patient-specific bone-implant mesh extends beyond the bone, it also includes finite elements that span the outer surface of the bone; no attempt is made to explicitly mesh the finite details of the periosteal surface of the patient's bone. Second, inclusion of such surrounding material ensures that there is no distortion of any elements at the bone-implant interface or when attempting to connect a mesh of the implant to a mesh of the endosteal surface of a patient's bone. In some cases in which the patient's endosteal or periosteal bone has an unusual geometry—perhaps for a particularly small individual, or within an arthritis-degenerated bone, or with some unknown pathology, or in a very elderly, porous, or thin bone—the finite elements can become distorted when autopaving is used and in such cases either manual meshing or some other type of user interaction is required to rectify the element distortion or else a prohibitively large number of elements needs to be included in the model (which would compromise ease of use in a clinical setting). Even in more usual bone geometries, there can be problems with element distortion when attempting to automatically mesh about geometrically complex features on the implant surface such as screw threads, holes, fillets, or fenestrations, or the like.

Using the information on implant position from process 108, in process 110 the selected pre-constructed non-patient-specific bone-implant mesh is registered to the correct position with respect to the implant. Next, using the mask information from process 106, in process 111 the pre-constructed non-patient-specific bone-implant mesh is masked to remove all non-implant elements from the pre-constructed non-patient-specific bone-implant mesh that fall outside the periosteal surface of the bone. A conversion from pre-constructed non-patient-specific to patient-specific finite element mesh is then completed in process 112 wherein the material properties of the non-implant finite elements are assigned based on the gray-scale Hounsfield Unit data in the patient's CT scan 105. These gray-scale data are related to the attenuation of X-rays through the bone in proportion to the amount of bone mineral. Any imaging modality that similarly provides gray-scale data that is related to the attenuation of X-rays through bone mineral is well suited for such material property assignment. Such modalities include CT, DXA, and planar (digital) X-rays, including portable "C-arm" and "O-arm" imaging devices.

Figure 2:
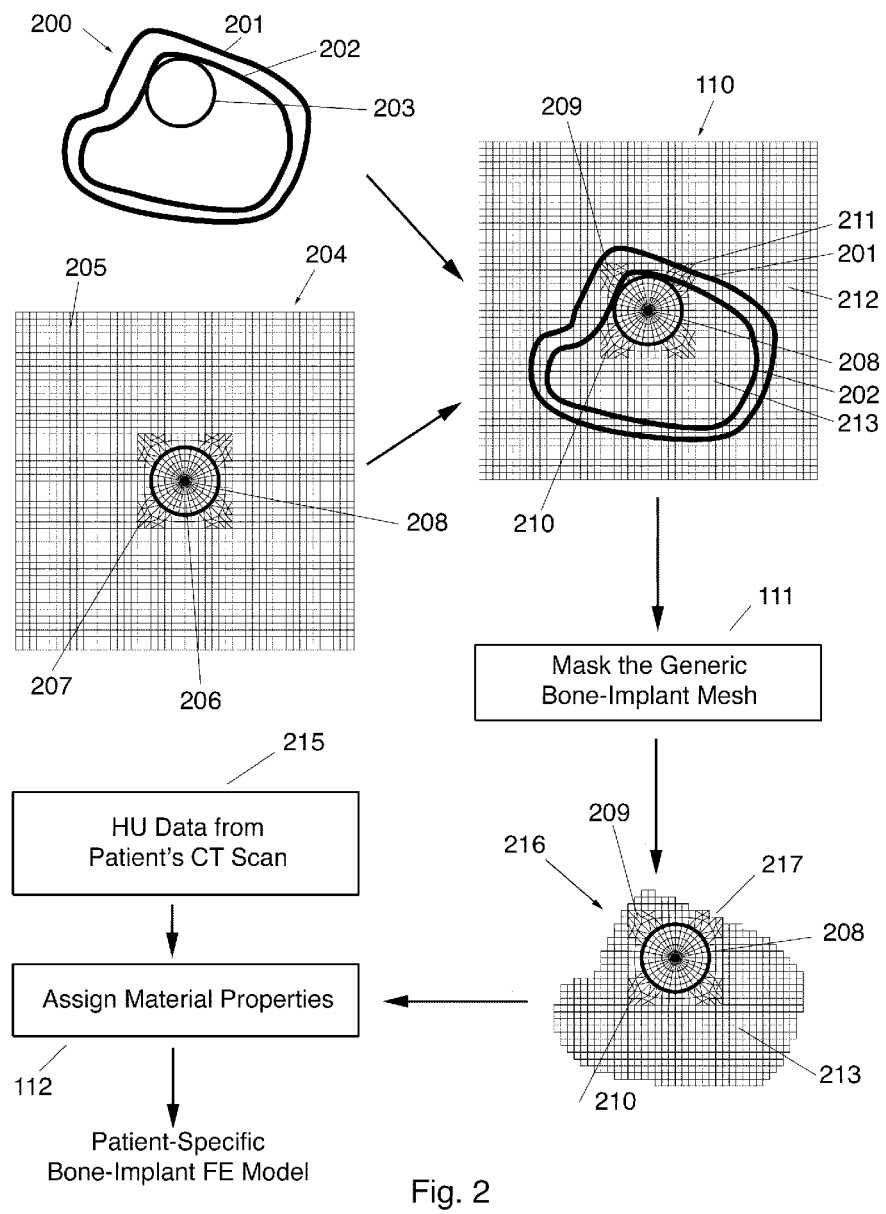
FIG. 2 is a schematic of the process of FIG. 1 of adapting a pre-constructed non-patient-specific bone-implant mesh into a patient-specific bone implant mesh, primarily based on masking of a pre-constructed non-patient-specific bone-implant mesh.

These details of step 103 are depicted graphically in FIG. 2 for a two-dimensional (2D) example, although nothing would differ conceptually for a three-dimensional (3D) application; it is understood that a 2D example is shown here for illustrative purposes only and in no way limits applicability of this invention to 2D analysis techniques. In 200, the position of the implant 203 is shown with respect to endosteal and periosteal bone surfaces 202 and 201, respectively. These surfaces were identified in process 106 as part of the segmentation process; in many applications, an endosteal surface may not be identified and implant positioning may depend only on periosteal position. Non-patient-specific bone-implant mesh 204 is large enough to fully envelop the bone. Pre-constructed non-patient-specific bone-implant finite element mesh 204 is shown for a circular cross-sectional implant, with outer surface 208 which corresponds exactly to the surface geometry of the implant 203 in 200. The thick nature of lines used to depict 208 is due to presence of a very thin layer of finite elements at the implant surface, used to enable detailed modeling of the bone-implant interface conditions. In this example, the pre-constructed non-patient-specific bone implant mesh contains a variety of different types of finite elements: most elements distant from implant are voxel-type elements 205, elements 207 in region just past surface of implant are triangular, and elements 206 within mesh of implant are curved quadrilateral.

In process 110, the pre-constructed non-patient-specific bone-implant mesh is registered to the digital image of the implant surface. Here it is seen that some elements 212 fall outside the periosteal bone surface 201 and other elements 213 fall within the endosteal bone surface 202, and some other elements 209 fall between the endosteal and periosteal bone surfaces. Elements 210 are triangular but are placed well within the bone whereas elements 211, also triangular, fall just outside the periosteal surface of the bone. After the pre-constructed non-patient-specific bone-implant is masked in process 111, all elements are discarded that fall outside the periosteal surface, resulting in mesh 216 having a patient-specific periosteal geometry. Thus, elements 211 are now discarded, revealing periosteal surface detail 217, whereas internal elements 209, 210, and 213 are all retained. Finally, the patient-specific finite element mesh of the bone-implant model is created in process 112 by assigning material properties to each non-implant finite element in mesh 216 based on the Hounsfield Unit (HU) data 215 in the patient's CT scan.

Figure 3:
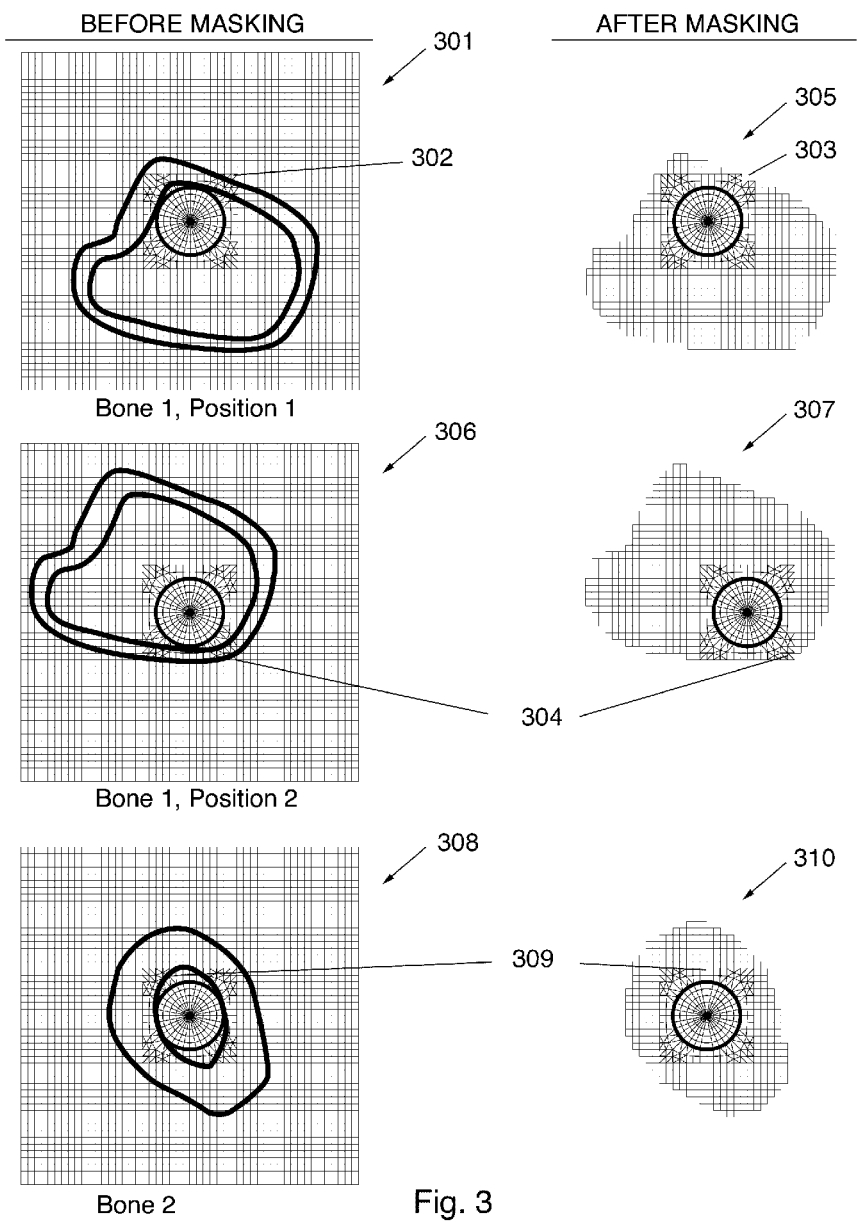
FIG. 3 shows an embodiment of FIG. 2, using the same pre-constructed non-patient-specific bone-implant mesh applied to differently-positioned implants in the same bone and to the same implant in different bones.

FIG. 3 shows masking process 111 applied to the same type of implant in different positions and/or bones, both before and after the masking. In this way, pre-constructed non-patient-specific bone-implant mesh 301 for a first bone with the implant in a first position is masked into a patient-specific mesh (material properties not yet assigned) 305; pre-constructed non-patient-specific bone-implant mesh 306 for the first bone with the same implant in a second position is masked into a patient-specific mesh (material properties not yet assigned) 307; and pre-constructed non-patient-specific bone-implant mesh 308 for a second bone with the same implant is masked into a patient-specific mesh (material properties not yet assigned) 310. Note that triangular elements 302 in pre-constructed non-patient-specific mesh 301 are masked to reveal surface detail 303, whereas other triangular elements 304 are retained. For the example shown in FIG. 3, the periosteal geometry of the bone in mesh 305 is exactly the same as in mesh 307.

In mesh 310, elements 309 represent a gap in the bone and would be assigned very low material properties in process 112 since the HU gray scale values would also be so low. In this way, gaps around the surface of an implant can be implicitly captured. Alternatively, one could remove elements 309 in patient-specific mesh 310 when the gray scale HU values fell below a specified threshold. The versatility of the meshing technique is evident from these examples in FIG. 3 and it should be clear to one of ordinary skill in the art that the technique can be applied to any geometry implant in any geometry bone and that the technique is not limited to the specific type of meshes shown herein.

Returning to the overall method as depicted in FIG. 1, once the geometry of the bone-implant mesh has been masked to produce a patient-specific periosteal geometry for the mesh, material properties are assigned in process 112 as described above. Material properties of the actual implant and the constitutive properties of the bone-implant interface, e.g. no-tension contact with friction, are included in the description of the non-patient-specific mesh of the implant. Material properties for the adjacent tissue within the implant mesh and for the bone can be assigned based on the information in the CT scans or can be applied in a non-patient-specific fashion. For details of the former, see for example, U.S. Pat. No. 5,172,695 ("Method for improved prediction of bone fracture risk using bone mineral density in structural analysis"). Other known methods in the art may also be used for assignment of material properties, such as by assigning material properties at each Gauss point within the finite element rather than by averaging material properties to the whole element.

By basing material properties of such "adjacent tissue" from the CT scans, very low modulus properties will be assigned to regions that represent a gap between the actual implant and bone, and high modulus properties can be assigned to regions where there is contact between the actual implant and bone. By varying the size of the elements of the adjacent tissue within the pre-constructed non-patient-specific bone implant mesh, one controls the fidelity to which gap regions can be described in the models. This implicit approach circumvents the need to create meshes of the bone and actual implant that explicitly account for variable gap regions between implant and bone—a very difficult feature to include in any automatic mesh generator that would reliably work for all possible bones in a clinical setting.

Finally, in process 113, loading and fixity boundary conditions are applied and a finite element analysis is performed. Typically, such boundary conditions are applied in a predetermined fashion and thus this step can be fully automated. The resulting patient-specific finite element analysis provides outcome measures for that specific patient that describe the relevant biomechanical characteristics of the bone-implant system under the prescribed loads and boundary conditions. An example of such is the overall displacement of the implant under a given applied force to the implant, a quantitative measure of implant stability. An alternative outcome would be the strength of the bone-implant construct under very high or hypothetical loading conditions. An example of this would be the axial pull-out strength of a pedicle screw. Measures of risk of local failure of the bone could also be output.

Other outcomes can be used, depending on the clinical application. For example, when using non-linear interface contact conditions with friction between the implant and surrounding tissue, a quantitative measure of relative motion between the bone and implant could be particularly useful in identifying implants at high risk of inducing formation of soft fibrous tissue in the long-term. Typically in performing such finite element analyses of bone-implant systems, it is important to include non-linear no-tension and frictional interface conditions between the implant and bone. These interface conditions are contained within the description of the non-patient-specific mesh for the implant. To produce these outcomes, process 113 may contain more than one actual finite element analysis on any given patient-specific finite element model. For example, a linear analysis might be first performed to estimate stiffness of the bone-implant structure, a nonlinear contact analysis then performed to estimate relative displacement between bone and implant, and others.

The result of the patient-specific finite element analysis can be written to a medical report 114 for the patient, to a digital data file, or can be displayed directly on a computer terminal for intra-operative use. In studies comparing the biomechanical behavior of different implants in a plurality of bones, the entire process can be repeated for each different bone, and results can be written to a data file on a computer or the like.

Figure 4A:
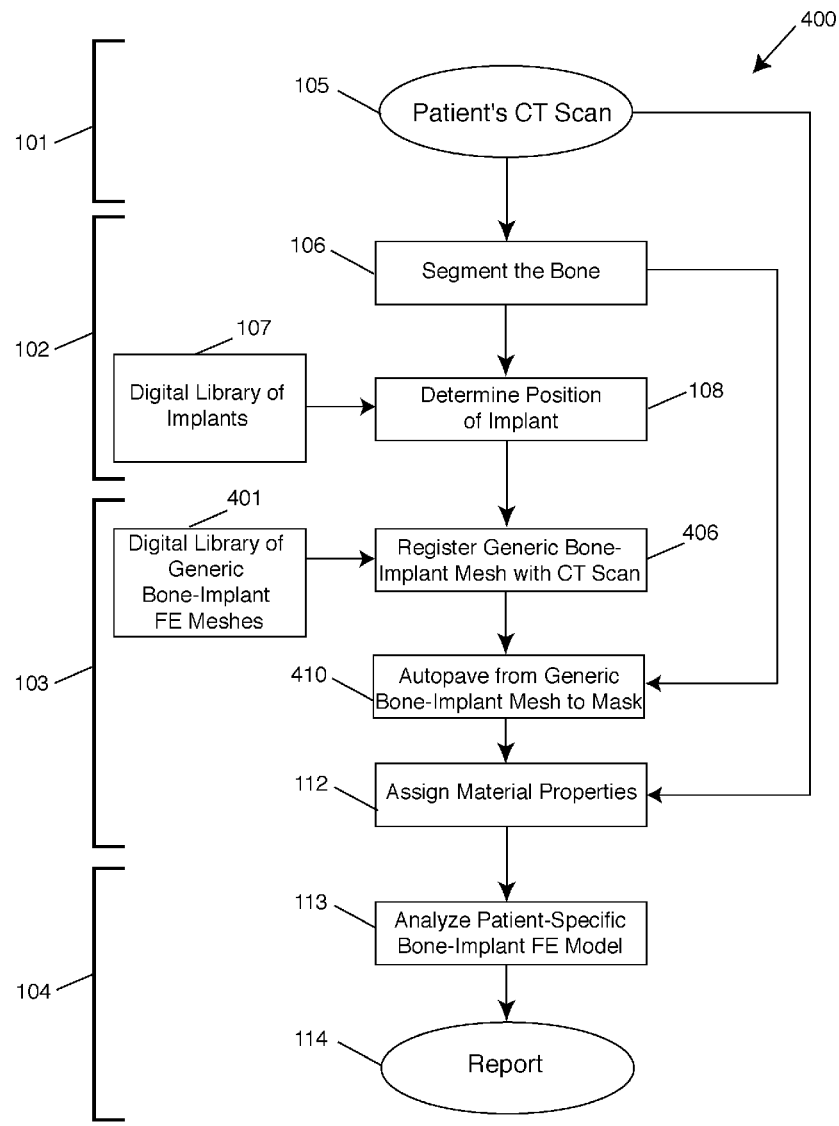
FIG. 4a is a flowchart of another preferred embodiment of the method, primarily based on a combination of autopaving and masking.
Figure 4B:
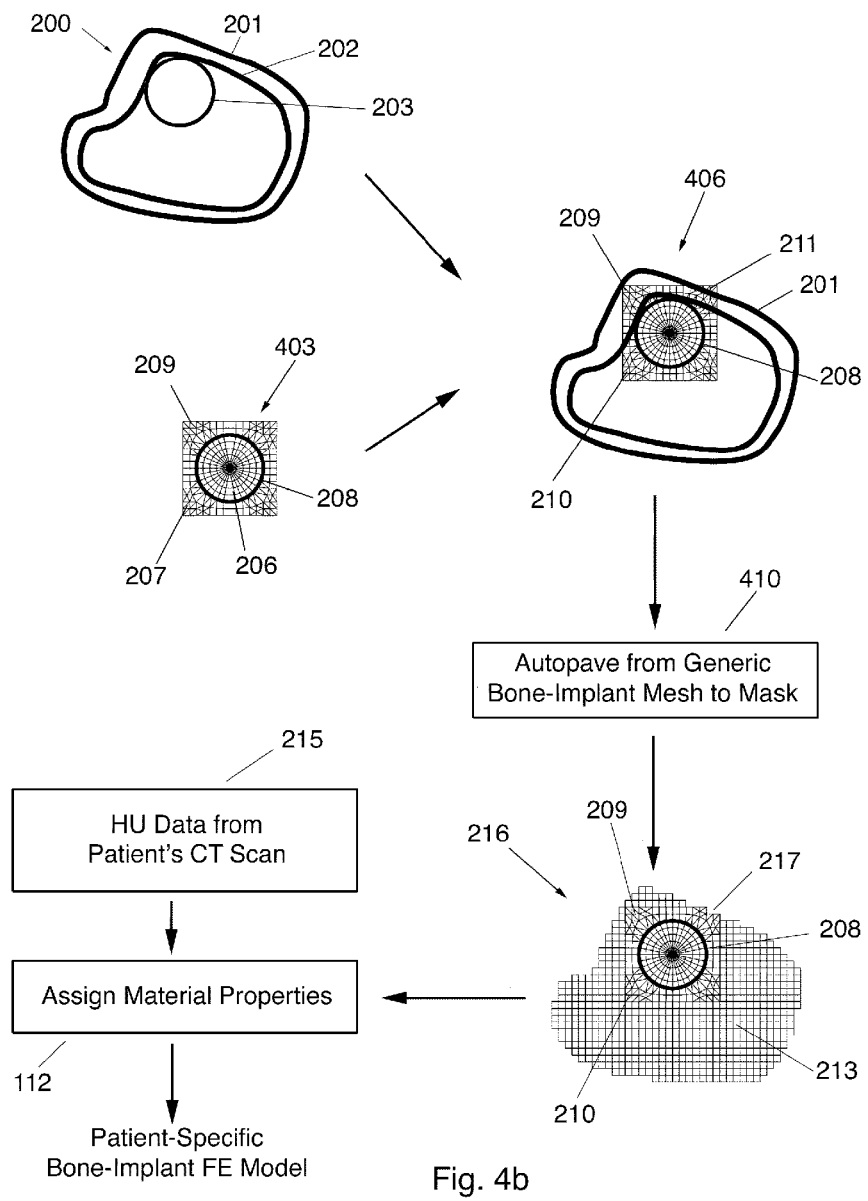
FIG. 4b is a schematic of the process of FIG. 4a of adapting a pre-constructed non-patient-specific bone-implant mesh into a patient-specific bone implant mesh, primarily based on a combination of autopaving and masking.

In an alternative embodiment, as depicted in FIG. 4a and FIG. 4b, the pre-constructed non-patient-specific bone-implant finite element mesh 204 of FIG. 2, which extends beyond the periosteal surface, is replaced by pre-constructed non-patient-specific bone-implant finite element mesh 403, which extends beyond the implant surface 203 and into the surrounding bone but not necessarily beyond the periosteal surface of the bone 201. As a result, process 111 of FIG. 2 is replaced by process 410, in which a patient-specific bone-implant mesh is created by autopaving (i.e. using an automatic mesh generator, which would generate volumetric elements for a 3D model or planar elements in a 2D model) from the surface of the non-patient-specific bone-implant mesh to the mask of the periosteal surface of the bone, as described in the image-processed CT image from process 106. In addition, the digital library of pre-constructed non-patient-specific bone-implant meshes 401 now contains a different type of pre-constructed non-patient-specific bone-implant mesh than the digital library 109 of the first embodiment shown in FIG. 2.

The finite elements of the pre-constructed non-patient-specific bone-implant mesh within and adjacent to the implant for this alternative embodiment can be exactly similar to those in the embodiment shown in FIG. 2, namely, pre-constructed non-patient-specific bone-implant finite element mesh 403 is shown in FIG. 4b. for a circular cross-sectional implant, with outer surface 208 which corresponds exactly to the surface geometry of the implant 203 in pre-constructed non-patient-specific bone-implant mesh 200 that extends beyond the periosteal surface. The thick nature of lines used to depict 208 is due to the presence of a very thin layer of finite elements at the implant surface, used to enable detailed modeling of the bone-implant interface conditions and possible presence of small gaps. In this alternative embodiment, the pre-constructed non-patient-specific mesh contains a variety of different types of finite elements: elements 207 and 209 in regions just past the surface of implant are triangular and elements 206 within mesh of implant are curved quadrilateral; other elements within the envelope of the pre-constructed non-patient-specific bone-implant mesh are voxel-shaped.

Referring to FIG. 4b, in process 406, the pre-constructed non-patient-specific bone-implant mesh 403 is registered to the digital image of the implant surface. Here it is seen that some elements in the pre-constructed non-patient-specific bone-implant mesh 211 fall outside the periosteal bone surface 201 and some other elements 209 fall between the endosteal and periosteal bone surfaces. Elements 210 are triangular but are placed well within the bone whereas elements 211, also triangular, fall just outside the periosteal surface of the bone. In process 410, autopaving is used to complete the mesh from the surface of the pre-constructed non-patient-specific bone-implant mesh to the periosteal surface of the bone, using the mask information from process 106. The finite element mesh may be completed by autopaving from the surface of the pre-constructed patient-specific bone-implant mesh to the periosteal surface of the bone mask. A masking process is then performed in which any non-implant elements 211 in the pre-constructed non-patient-specific bone-implant mesh that fall outside the periosteal surface are discarded. This results in mesh 216 having a patient-specific periosteal geometry. Thus, elements 211 are now discarded, revealing periosteal surface detail 217, whereas internal elements 209 and 210 are retained and autopaved elements 213 are also included. Finally, the patient-specific finite element mesh of the bone-implant model is created in process 112 by assigning material properties to each non-implant finite element in mesh 216 based on the Hounsfield Unit (HU) data 215 in the patient's CT scan.

For the example shown in FIG. 4b, voxel-type hexahedral elements were autopaved. It should be clear that any type of element could be used for the autopaving, tetrahedral elements being a good alternative to voxels or hexahedral elements. It is noted that the final patient-specific mesh in the embodiment shown in FIG. 2 is, in some embodiments, exactly the same as the patient-specific mesh in the embodiment shown in FIG. 4b. However, these meshes may differ if a non-voxel type of autopaver were used instead in the latter embodiment. It should be clear also that this embodiment would also be applicable when one instead wanted to autopave to the endosteal surface of the bone, the inside surface of the cortical bone, or some other internal surface of the bone, instead of to the periosteal surface. In such cases, a complete mesh of the bone could be achieved by then meshing from such internal surface to the periosteal surface or by adding a layer of outer finite elements representative of the cortex.

In a related, alternative embodiment, one could first autopave the entire mask, remove a volume of elements from this mesh, and then replace that volume with the pre-constructed non-patient-specific bone-implant mesh. This option is particularly useful when the external boundary of the pre-constructed non-patient-specific bone-implant mesh coincides with the boundaries of elements in the autopaved mesh. This is oftentimes possible to achieve when the autopaving is done with voxel elements and when, by appropriate registration of the bone image, the coordinate system of such voxel elements is chosen to coincide with the external sides of the pre-constructed non-patient-specific bone-implant mesh. When the boundaries of these meshes do not coincide, and when unmeshed regions exist after the volume of elements is removed from the autopaved mesh of the entire mask, the pre-constructed non-patient-specific bone-implant mesh can be connected to the autopaved mesh by a second autopaving process. Regardless of how the autopaved mesh of the mask is combined with the pre-constructed non-patient-specific bone-implant mesh, as with the other embodiments, any non-implant elements are then removed by masking to arrive at the patient-specific bone-implant mesh.

Figure 5:
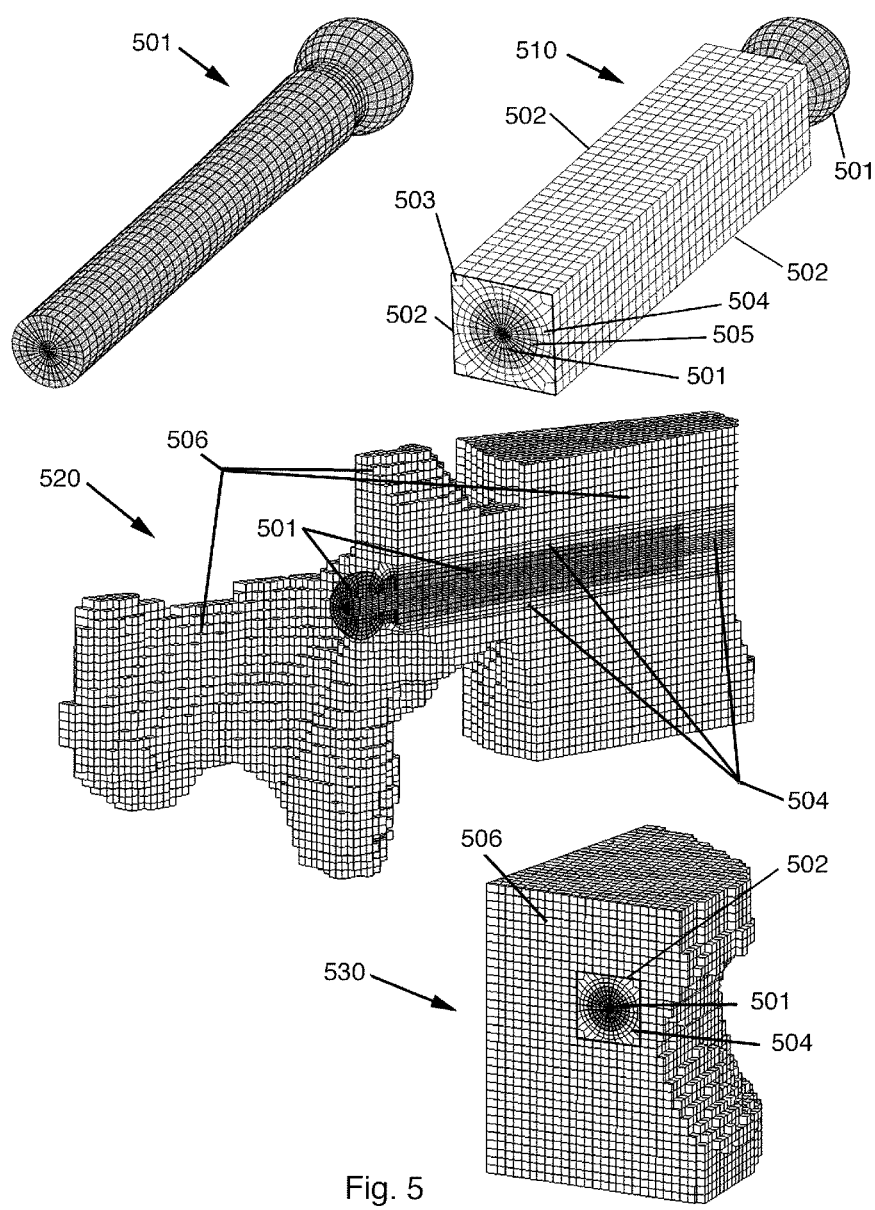
FIG. 5 shows another preferred embodiment, in which autopaving of the full mask is combined with replacement of a volume of autopaved elements by pre-constructed non-patient-specific bone-implant mesh.

FIG. 5 shows an example of this embodiment in which implant finite element mesh 501 represents a vertebral pedicle screw (threads not shown for illustrative purposes). For this specific implant, the corresponding pre-constructed non-patient-specific bone-implant mesh 510 comprises finite elements 505 representing the implant surrounded by a volume of finite elements 504 representing the surrounding material, these finite elements being a variety of hexahedral-shaped elements, some elements 504 and 505 with curved sides and other elements 503 with straight sides. Importantly, the pre-constructed non-patient-specific bone-implant mesh 510 has an external box shape. The external envelope 502 of the pre-constructed non-patient-specific bone-implant mesh has a regular grid of elements, specifically designed to be compatible with a voxel-based autopaver. A patient-specific finite element model 520 is easily produced by adding finite elements 506, from an original voxel-autopaving of the mask obtained from process 106. For illustrative purposes, the section of the model 520 shows the mesh detail in a plane taken through the center of the implant, and only one half of the vertebra (and one pedicle screw) is shown. Further section 530 reveals a different cross-sectional plane through the model, and shows envelope 502 of the non-patient-specific bone-implant mesh, which is almost indistinguishable from the surrounding autopaved voxel finite elements. In the example shown in FIG. 5, each autopaved voxel element has a dimension of 1 mm. Larger or smaller elements could be used depending on the numerical convergence characteristics of the problem at hand. Such mesh characteristics would also be reflected by the size of elements in the non-patient-specific bone-implant mesh—and all such considerations are resolved in advance of any clinical application.

The pre-constructed non-patient-specific bone-implant meshing method disclosed in this patent may not, in some cases, accurately describe the true periosteal geometry of the bone because the process of masking the pre-constructed elements at the outer bone surface may lead to jagged edges in some regions, particularly when voxel-type elements are used. This limitation should introduce only minor errors in analysis of bone-implant systems because the most critical behavior of such systems is associated with the behavior of the bone-implant interface and its environs; this behavior is relatively insensitive to the precise geometry of the periosteal surface. However, when such errors are of concern, they can be mitigated by reducing the size of the elements in the pre-constructed non-patient-specific bone-implant mesh.

In clinical application to surgical planning, the patient-specific finite element analysis is preformed under a prescribed set of loading conditions and a biomechanical outcome is computed. Boundary conditions can be applied automatically to the patient-specific finite element mesh by a number of known methods in the art. Typical outcomes of the finite element analyses could include relative motion between the bone and implant, maximum stress level in the bone adjacent to the implant, overall stiffness of the bone-implant construct, or strength of the bone-implant interface. While the precise outcome used and how it is interpreted clinically will depend on the specific clinical application, the disclosed method can be used to generate patient-specific models suitable for a wide variety of clinical applications.

Figure 6:
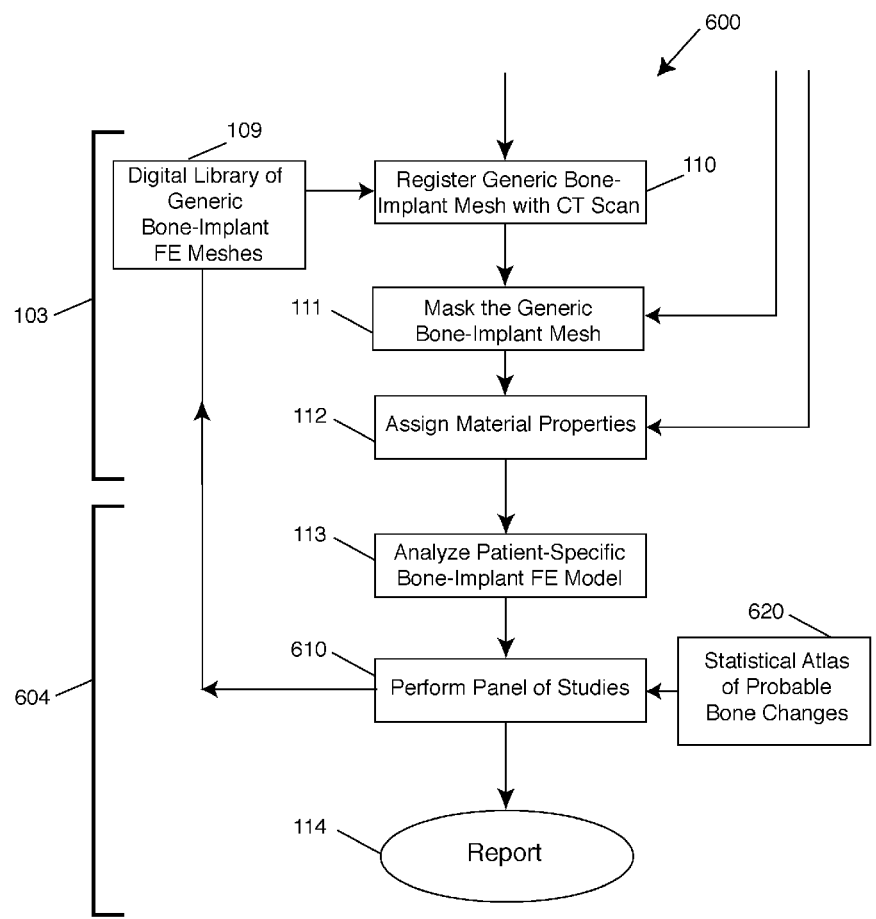
FIG. 6 is a schematic of the method of performing an automated panel of studies to generate additional patient-specific data for improved surgical planning.

In an improved application of this method to orthopaedic-type surgical planning, shown schematically in FIG. 6, what was fourth step 104 in FIG. 1 is now an expanded step 604. Specifically, after finite element analysis step 113 is completed but before medical report 114 is prepared, a panel of additional finite element analyses 610 is automatically performed in order to provide additional outcomes for improved surgical planning. This panel of studies is achieved by prescribing a set of pre-defined variations of the finite element models and then re-running the finite element analyses using these altered properties and comparing results across these parametric analyses.

In one such embodiment, the size of the implant is increased by one increment by choosing a larger implant from the library of implant meshes 109; a second non-patient-specific bone-implant mesh is analyzed for this newly-sized implant. A smaller sized implant is then modeled by choosing a smaller implant from the library of implant meshes 109; a third non-patient-specific bone-implant mesh is then analyzed for this newly-sized implant. Results for the three implant sizes are compared to determine an optimal implant size determined by appropriate interpretation of these data by the surgeon. When the particular implant design has more than one size parameter, additional studies could be performed varying the other size parameters appropriately.

Figure 7:
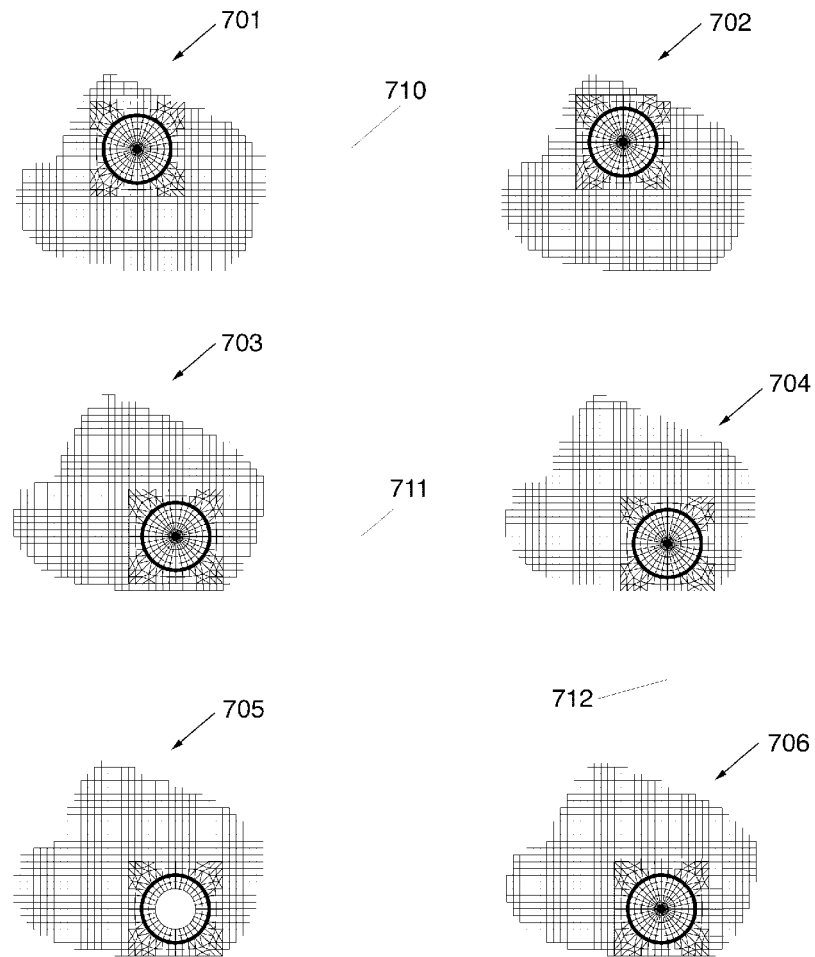
FIG. 7 shows application of such a panel of studies: much different positions of the same implant in the same bone; slightly different positions of the same implant in the same bone; and a different implant design with the same position in the same bone.

In another embodiment, shown schematically in FIG. 7, the implant position could be varied by a preset amount in various planes. Referring to FIG. 7 and using horizontal line 710 as a visual guide, it is seen that patient-specific bone-implant mesh 701 has the implant positioned one voxel below the implant in patient-specific bone-implant mesh 702, although both finite element models have the same periosteal surface of the bone. Similarly, using horizontal and vertical lines 711 and 712, respectively, as visual guides, it is seen that patient-specific bone-implant mesh 704 has the implant positioned one voxel below the implant in patient-specific bone-implant mesh 703; and patient-specific bone-implant mesh 706 has the implant positioned one voxel to the left of the implant in patient-specific bone-implant mesh 704, although in all cases the finite element models have the same periosteal surface of the bone. In each case, process 112 would be carried out after creating such patient-specific geometric meshes in order to create new patient-specific finite element models for each case. After rerunning a number of such analyses, an optimal implant position could be identified based on a comparison of the biomechanical outcomes of interest from the multiple finite element analyses.

In another embodiment, a different implant design could be assessed by automatically choosing an alternative implant design from the library of pre-constructed non-patient-specific bone-implant meshes 109. This is show schematically in FIG. 7, in which patient-specific bone-implant mesh 705 has a hollowed out implant compared to the otherwise same patient-specific bone-implant mesh 706 that has a solid implant. It is understood that any different type of implant geometry could be swapped out in this application. It is noted that when the embodiment shown in FIG. 4 and FIG. 5 is used, it should be possible to have the same external envelope on the pre-constructed non-patient-specific bone-implant mesh while having different implants contained therein. In this way, running a panel of studies with different implant designs only requires swapping out the pre-constructed non-patient-specific bone-implant mesh from the patient-specific implant mesh, thus speeding up overall analysis time by not requiring processes 406 or 410 to be repeated. Material properties will likely need to be reassigned in process 112, particularly when the surface of the implant is altered. Swapping out the pre-constructed non-patient-specific bone-implant mesh for one implant in a given bone and replacing it with another pre-constructed non-patient-specific bone-implant mesh for a different implant in the same bone is particularly useful when comparing the biomechanical behavior of different implants in a plurality of bones (discussed in more detail below). In such cases, if each patient-specific bone mesh, not including the volume of elements associated with the pre-constructed non-patient-specific bone-implant mesh, is saved after it is registered after a first analysis with a first implant, then that bone can be used for any number of subsequent analyses for the same general type of implant, e.g. a pedicle screw. Saving each such patient-specific bone mesh for a plurality of bones can then provide a library of such patient-specific bone meshes for future analysis. In this way, once a plurality of bones are used for analysis of any one implant, the same plurality of bones can easily be used for analysis with a different type of the same class of implant. This has the advantage of avoiding any need to register or mask the patient-specific bone meshes before virtual insertion of the implant via incorporation of the non-patient-specific bone-implant mesh.

In another embodiment, which does not require changing the masked patient-specific finite element mesh 216, the panel of studies could alter only the material properties of the bone in order to simulate the effects of aging, disease, drug therapy, or an added biologic agent intended to promote new bone growth or bone-implant tissue generation. For example, therapy could be simulated before implantation of the implant, in order to assess the benefits, if any, of delaying surgery in the event the bone is too weak for immediate implantation. Or, the effects of therapy could be simulated for an implanted bone in order to assess any added benefit of treating the patient with the therapeutic agent after surgery. Biologic effects of tissue integration or bone ingrowth into the implant could be assessed by alteration of the interface properties between the bone and implant, as well as alteration of the material properties of the interface tissue adjacent to the implant. Loosening of the implant from the bone could also be simulated following a similar strategy, in which the material properties of the tissue adjacent to the implant are altered. Such alterations could be prescribed in advance via the material property descriptions in the pre-constructed non-patient-specific mesh of the implant. Or, a prescribed numbering of the finite elements within the pre-constructed non-patient-specific mesh of the implant could be used to facilitate parametric variation of these material and interface properties within the pre-constructed non-patient-specific bone implant mesh.

Referring to FIG. 6, in performing a panel of studies in which the material properties or geometry of the patient's bone are altered for the purposes of surgical planning, rather than simply use some non-patient-specific changes, a more patient-specific alteration can be achieved by using a statistical atlas of such probable changes 620 as an additional input in order to prescribe the most probable patient-specific changes. In this embodiment, a statistical atlas describes statistically typical temporal changes that occur in the relevant general population, as measured by pairs of equal-quality CT scans taken at two time points in the relevant population. All such CT scans are mapped to a master bone, using deformable registration or its equivalent. Within the master bone, it is then possible to quantify location-specific changes in bone density for the entire population and describe that using statistical measures. For example, one can measure the mean change across the population and its standard deviation at each sampling point within the master bone. Known techniques for development of such voxel-based statistical atlases of bone changes can be used (see, for example, Li W, Kezele I, Collins D L, Zijdenbos A, Keyak J, Kornak J, Koyama A, Saeed I, LeBlanc A, Harris T, Lu Y, and Lang T, Bone 41: 888-895, 2007).

Additionally, should such relations be shown to exist, such changes can be related to such patient factors as age and sex, as well as the local measures of density within the CT scan. In this way, a statistical atlas of bone changes can be developed to describe typical changes with age within the relevant population, and such atlases can also be developed for prediction of likely changes induced by specific therapeutic treatments, such as drug treatment. The resulting statistical atlas of bone changes describes most probable changes in local density at a specific location within the bone given information in the patient's CT scan, as well as patient sex, age, body weight, and perhaps other factors. Well known principles of machine learning, including statistical inference, are used to train the system for these purposes.

Specific surgical planning applications of the disclosed method include but are not limited to the following:

Analysis of biomechanical stability of fracture fixation implants about a healing bone. In this case, the adjacent tissue within the pre-constructed non-patient-specific mesh of the implant could be assigned material properties representing fibrous tissue, callus, or calcified bone, depending on the appearance of such material on the patient's CT scan. Once the patient-specific mesh is generated, boundary conditions could be applied to simulate habitual activities such as walking, and sporadic loading such as twisting and torsional loading, could also be included. The panel of studies could include assessment of maximum stability, by transforming the material properties of all adjacent tissue into stiff bone. This would provide a measure of bone-implant stability in a best-case scenario of healing, for comparison purposes with any current measure of stability. Another panel of studies could vary location of plate fixation to assist the surgeon in choosing how many screws to use for fixation and where to apply. Different sized plates could also be investigated, as well as the use of a titanium versus stainless steel plate.

Analysis of pullout strength of a pedicle screw in the spine, as well as the risk of bone failure and implant loosening for habitual loading, for spine fusion surgical planning. The panel of studies could include using a size up and down on the initially chosen screw design in order to provide a quantitative measure of stability for the purposes of sizing the screw by the surgeon. Simulation of drug treatment could be performed to assess affect of any response to drug treatment from a biomechanical perspective of implant stability. Screws could be chosen based on maximum implant pullout force. This test could also be used to assess if risk of loosening under habitual loading is too high for a specific patient. If so, alternative screw designs could be evaluated in an optional panel of studies, or, by repeating entire analysis by choosing a different screw design and re-running the analysis. Because this process is fully automated, the entire process could be preformed intra-operatively using CT scans obtained by appropriately calibrated "C-Arm" and "O-Arm" devices.

Choice of hip implant stem for total hip arthroplasty. Gaps between the implant and femoral diaphysis would be captured in this application by assigning very low material properties to the adjacent tissue within the patient-specific bone implant mesh as determined by the low density nature of gaps as measured in the CT scans. Non-linear interface elements between adjacent tissue and implant could also be included in the pre-constructed non-patient-specific bone implant mesh to allow frictional contact as well as separation of implant from bone in regions of tensile normal stress at this interface. Different implant sizes (one size up, one size down) could be analyzed for optimal implant sizing. Cemented versus cementless fixation could also be assessed. For the former, the interface tissue within the pre-constructed non-patient-specific bone-implant mesh would contain a layer of PMMA bone cement, in addition to an outer layer of tissue, the latter assigned material properties based on the data in the CT scan.

Other applications could include analysis of the tibial component of total knee replacements, spine fusion devices, and various pins and screws used for fixation of both implants and stabilization of fractures. Since dental implants are often attached to bone, the invention would be useful also in surgical planning and other applications in dentistry. Beyond direct clinical application, the method is also useful for the purposes of implant design, and provides a powerful means to compare the biomechanical performance of different types of implants for the same surgical indication. Such comparative performance can be used to choose among competing implants and assess relative efficacy. The invention is not limited to these specific applications as the use of this disclosed method for other bone-implant applications will be readily apparent to one of ordinary skill in the art.

The method provides new capabilities for comparing the biomechanical performance of a variety of different implant designs in a patient-specific manner, in a plurality of bones, for use in design and research studies. In performing such patient-specific analyses in a large number of bones, the variety of different implants could represent variations in design of a given implant, e.g. different values of a diameter, screw pitch, thickness, width, length, taper angle, any other geometric property, or a material property, and the like. The variety of different implants could alternatively represent different implants, e.g. competing pedicle screws from different manufacturers, competing femoral components of total hip replacement prostheses from different manufacturers, or different types of a given implant from a given manufacturer, e.g. a cementless vs. a cemented hip implant. Such a comparison could be performed as part of the engineering design process, and would be advantageous over the prior art because it would enable the design to consider the biomechanical performance of the implant in many different types of patient's bones. A database of medical images of bones, obtained previously by imaging live individuals, or as described above obtained from prior virtual analysis of an implant in a plurality of bones according to the specifications described above, could be used for such purposes, said database containing different types of bones (e.g. L1 or L2 vertebral body; proximal femur; proximal tibia), for both men and women, and covering different age ranges. Cadaver bones could also be imaged for such purposes, and doing so would enable higher resolution images to be obtained than might be possible when imaging live people. It is also possible to virtually alter said set of bone images to simulate possible or observed effects of aging, disease, and treatment. Said database could be used to perform such patient-specific comparisons in a standardized manner, such that a variety of different implants could be compared using the same set of bones. The term "patient-specific" is used in this type of application to mean an analysis based on an image of a particular bone, regardless of the source of that bone (human, animal, or cadaver) or how it was imaged (high or low resolution, clinical or research scanners, or scanning modality).

Alternatively, such a patient-specific comparison could be performed to compare relative effectiveness of competing implants in an attempt to identify what may be superior clinically among competing clinically-available devices. Such head-to-head comparisons are generally unfeasible clinically due to the huge cost of running the required large and long-lasting clinical trials. They are also unfeasible using cadaver experiments due to the relative scarcity of the amount of cadaveric bones required for a statistically valid comparison. The method would enable such comparisons to be made using hundreds of bones in a relatively inexpensive manner; plus, each bone can serve as its own control since a number of different implants can be virtually inserted and stressed in the same bone whereas this is not feasible in cadaveric studies since implantation of one implant into a bone likely compromises the bone integrity for any further implantation. Also, different types of loading conditions can be used in such comparisons to provide a rigorous biomechanical comparison. Such virtual patient-specific comparisons in many bones have never been made in the prior art because of the lacking of an automated meshing technique that would make such studies technically feasible in a reasonable amount of time and using a reasonable amount of resources and as applied to many different bones. Embodiments of the current invention overcome such obstacles and make such studies feasible.

Figure 10:
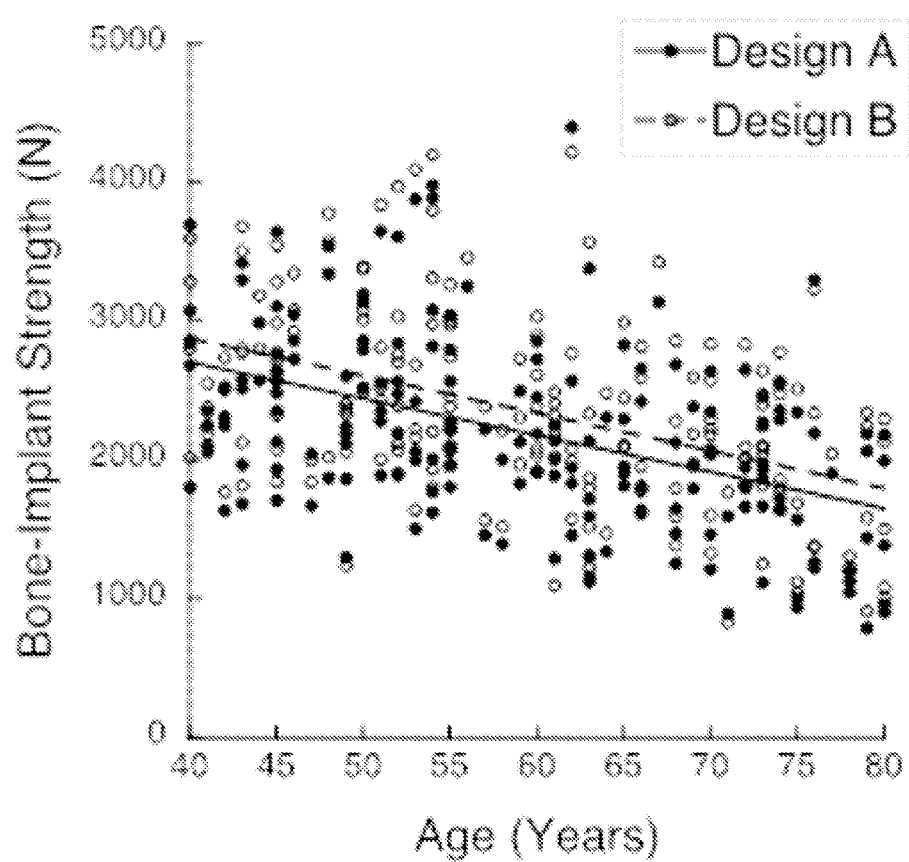
FIG. 10 illustrates a computed bone-implant strength of a pedicle screw virtually implanted in 183 L3 human vertebrae for two design configurations (designs A and B)
Figure 11:
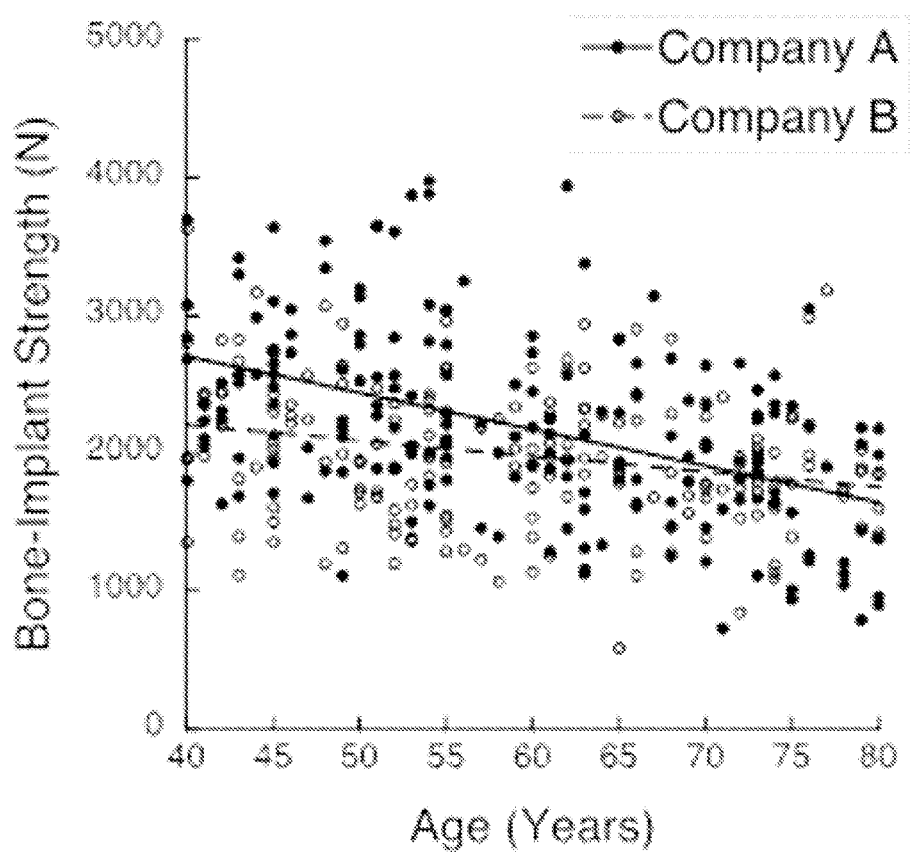
FIG. 11 illustrates a computed bone-implant strength for the same bones as described in FIG. 10 for competing pedicle screws available from two different companies (company A and B).

To illustrate examples of such applications of patient-specific comparisons in a plurality of bones in which a large number of bones is used, FIG. 10 illustrates a computed bone-implant strength of a pedicle screw virtually implanted in 183 L3 human vertebrae for two design configurations (designs A and B), and FIG. 11 illustrates the computed bone-implant strength for the same bones for competing pedicle screws available from two different companies (company A and B). In both cases, the bones were scanned previously using CT in a variety of patients and stored in a database for later use in such research studies. The bones were masked, and then the implants were virtually positioned and placed within each bone; finite element meshes were created by combining a patient-specific mesh of the bone with a pre-constructed non-patient-specific bone-implant mesh according to the specifications described above, and virtual loading was performed to provide biomechanical measures of bone-implant strength. Results from such analyses were then plotted on a graph against the age of each virtually assessed bone. Age is an example of a demographic parameter, defined for the purposes of this application as any measure that characterizes some aspect of the person associated with the virtually simulated bone. Plotting results of the biomechanical analysis in this way is of interest from a clinical perspective; other demographic variables include but are not limited to weight, height, sex, ethnicity, body-mass-index, and so forth. A demographic parameter in this context could also include other quantitative measures of the bone structure, including its density, cross-sectional area, height, or some other physical attribute of the bone or person that could have clinical or biological relevance. As shown in FIG. 10 and FIG. 11, virtual stress testing and presentation of results in this way demonstrates the substantial heterogeneity of bone-implant strength across different patient bones. By evaluating these two design options in so many bones, it is possible to detect a statistically significant strength advantage of Design A over Design B; it is also seen that the pedicle screw from Company A has an advantage of the screw from Company B in young patients but not in older patients. Such subtle but potentially clinically important distinctions would not have been possible by evaluation in a much smaller sample of bones, demonstrating a unique advantage of making such comparisons virtually in a patient-specific manner in a large set of bones. Once this analysis is performed, the finite element meshes for all registered bones, not including the non-patient-specific bone-implant mesh, can be saved in their registered coordinate systems for analysis of other implants in the same class. To analyze a different implant, the non-patient-specific bone-implant mesh for that implant is simply placed into the finite element meshes for all registered bones and the analyses can quickly be re-run for the new implant.

To further improve the level of automation for successful clinical application or when comparing different implants in a plurality of bones, in another embodiment step 102 (in FIG. 1 and FIG. 4*a*) for the sizing and positioning of the implant within the bone can employ automated deformable registration. Surgical planning 3D viewing software suites have been developed to help surgeons properly size and place an implant in a 3D medical image of a patient's bone, for example using CT scans. In such systems, the surgeon interacts with the system to view the patient's bone and virtually places the implant in the bone using their own best judgment, perhaps assisted by computer algorithms. Such techniques could be used in step 102 to position the implant in this invention. Alternatively, the use of a statistical atlas and deformable registration, as disclosed here, would enable automated sizing and positioning of the implant based on some accepted criteria and with appropriate training of the system. When desired, a surgeon or other expert could then view the resulting position and sizing of the implant and make adjustments before proceeding with the biomechanical analysis.

Figure 8:
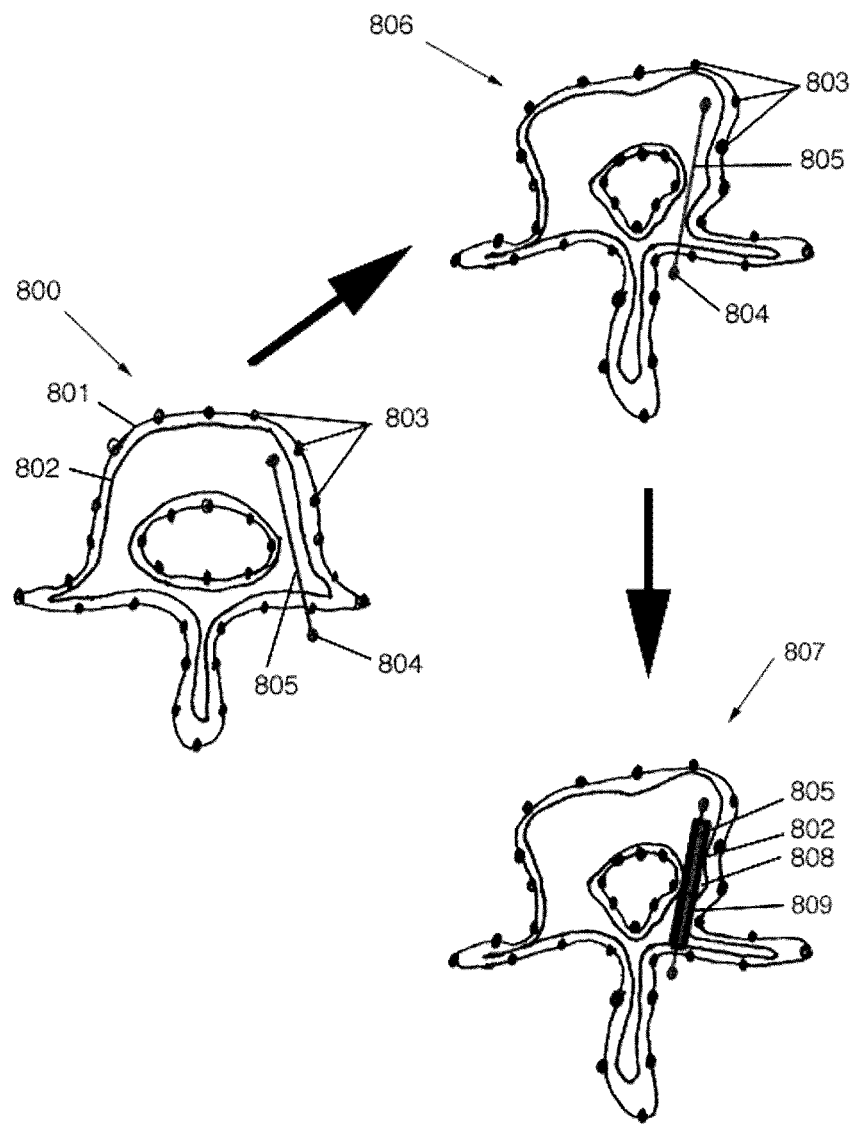
FIG. 8 is a schematic representation of the deformable registration, used for automated virtual positioning of the implant within the bone.

Referring to FIG. 8, the purpose of the deformable registration when used in step 102 (of FIG. 1 and FIG. 4*a*) is to virtually position and size the implant within the patient's bone in an automated fashion. It also provides positional and registration information that is subsequently used to register the pre-constructed non-patient-specific bone-implant mesh with the medical image of the patient's bone. Rigid and deformable (or elastic) registration techniques are well known in the fields of computer vision and advanced medical image processing. Such rigid and deformable registration techniques are applied to the image of the patient's bone in order to map it to a "master bone" image 800, derived from analysis of a statistical atlas of similar bone types. The statistical atlas mathematically represents the appearance of such bones in the clinically relevant patient population. Such master bone contains landmarks 803, previously chosen, that are used to position and size the implant. This statistical atlas-based deformable registration process is also used to segment and threshold the image to produce a bone mask, although alternate image-processing methods can also be used for such purposes. The bone mask is used subsequently in the creation of the patient-specific bone-implant mesh.

The type of implant to be analyzed is chosen from a digital library of implant images 107 (see FIG. 1). These images may contain all the relevant geometric features of the implant required for proper sizing and positioning and also contain mathematical landmarks on the bone. The deformable registration uses mappings of said landmarks from the master bone to the patient's bone to initially size and position the implant within the patient's bone. Additional refinements can be made to the size and position using pre-constructed criteria associated with the geometry and density of the bone and proximity of implant to such landmarks. Only sizes (and designs) of the implant that are contained in the digital library of implants 109 are admissible in this process.

In one embodiment of a fully automated process, as depicted in FIG. 8, the implant is initially placed based on rigid body and deformable registration techniques using a master bone and bone and implant axis landmarks, and the implant is then finally placed and sized using pre-defined criteria that account for the proximity of pedicle surfaces to the implant surface and quantification of local bone density. As shown schematically in FIG. 8, master bone 800 is a human vertebral body, a cross-section of which is shown schematically to contain an outer cortical surface 801 and an inner cortical surface 802. Landmarks such as points 803 are placed by prior analysis of said master bone. Such landmark points can be on outer and/or inner surfaces of cortical bone, and may also include internal points based on density of the internal trabecular bone. For purposes of clarity, only some landmarks 803 on outer cortical surface are shown in FIG. 8. In practice, the number of landmarks could vary from less than 10 per cross-section to more than a few hundred. Also, FIG. 8 depicts a two-dimensional view of the bone, whereas in practice the process would typically apply to a fully three-dimensional model of the bone.

Central axis 805 of implant is appropriately placed in master bone, identified by landmark points 804 at either end of axis. Said master bone can be created from a statistical atlas using techniques known to those in the field of computer vision and image processing of medical images, or, can be created from a single representative bone. For the former, the shape of the idealized representation of the vertebra, as represented by the locations of the landmark points or some mathematical parameterization of them, is learned from a training set of vertebrae from the target clinical population. If instead a single representative bone is used, it could be chosen based on age and sex to represent subsets of the general population of direct relevance to the application and the patient under analysis. The master bone is then mapped using rigid body and deformable registration onto CT scan of the patient's bone 806. Landmark points 803 and 804 on the bone and implant axis, respectively, are mapped to corresponding locations on CT scan of patient's bone. Location and orientation of implant axis 805 are thus found for patient's bone. Such placement of implant axis may be constrained to ensure it conforms with certain landmarks on the bone, e.g. that the implant exits the bone in an appropriate location on the posterior elements. This represents an initial placement and sizing of the implant in the patient's bone.

Using criteria specific to the clinical application and optionally implant design, the final placement and sizing of implant is determined automatically by an optimization analysis on a more detailed geometric representation of the implant 807. Such criteria can consider factors other than landmark points, including density of the bone 808 local to the implant surfaces, proximity of implant surface to pedicle surfaces 809, or some combination of these and other factors. In one application, an optimization criterion minimizes the sum of distances from points on portion of implant surface to pedicle surfaces 809, subject to the constraint that the implant does not impinge the bone surface. Another placement criterion could maximize sum of local bone density 808 adjacent to the implant surface in the pedicle region. Variables in these optimization criteria could include both size and position of implant, and only implant sizes that exist in the digital library of implants 107 would be admissible.

Figure 9:
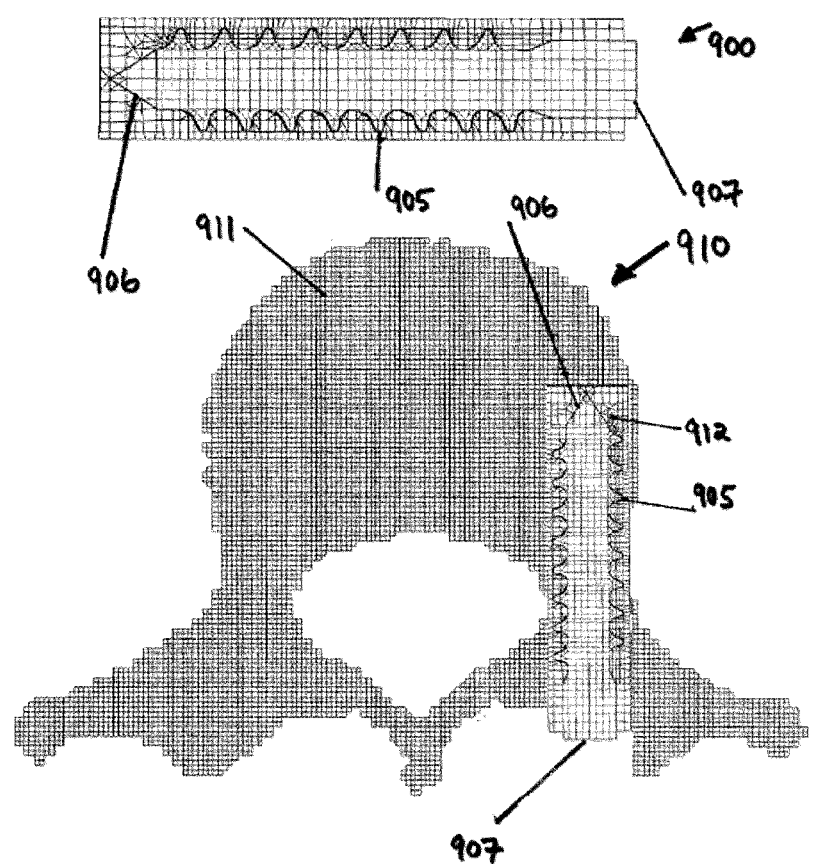
FIG. 9 shows the fine detail within the finite element mesh of an implant combined with a patient-specific finite element mesh of the bone.

One important feature of the method is that it allows incorporation of a highly detailed finite element mesh of an implant into a patient-specific model of a patient's bone. FIG. 9 shows an example of the method resulting in a detailed finite element mesh of a pedicle screw type of spinal implant, embedded within a vertebral body of an osteoporotic women. For illustrative purposes, only a 2D schematic is shown. The finite element mesh 900 of the pedicle screw includes such geometric fine detail as the screw threads 905, screw tip 906, and screw head 907. A combination of hexahedral and tetrahedral elements is used. Following the preferred embodiment of the method as shown in FIG. 1, the method produces a patient-specific bone-implant mesh 910, maintaining the detail of the screw threads 905, screw tip 906, and screw head 907. In this example, voxel-type hexahedral elements are used to mesh the bone 911 away from the implant, whereas a combination of non-voxel-type hexahedral and tetrahedral elements, some curved, are used to model the surrounding material 912 immediately adjacent to the implant surface.

The method can also be applied to situations in which multiple implants are used in the same bone. There are three general cases for such situations. The first is when the two implants are not in contact and are spaced relatively far from each other. An example of such is the placement of a pedicle screw in each of the two pedicles of a vertebra. In this situation, the method shown in FIG. 4b can be applied. First, the bone is divided into two segments by a cutting plane, each segment containing the pedicle and surrounding bone. A convenient cutting plane for a pedicle screw analysis is the mid-sagittal plane of the vertebra. Then, the method shown in FIG. 4b is applied to each bone segment, in which one of the masked surfaces of each bone segment is the cut plane; tetrahedral autopaving would be well suited for such purposes. The two resulting patient-specific finite element meshes can be mathematically joined using standard node-to-plane constraint elements applied at the cut plane or any equivalent means. Material properties can then be applied to all non-implant finite elements using the HU gray scale data in the CT scans, as described earlier.

Alternatively, when a number of elements in this autopaving approach are considered too high, the method shown in FIG. 2 could be applied to each bone segment, using voxel elements. The resulting layer of voxel elements directly along the cut plane in the models for each segment may not align. When not aligned, these layers could then be removed, and the two models are joined by autopaving the empty space between the two remaining meshes with tetrahedral elements. Since the volume to be autopaved in this instance would represent only a thin mid-sagittal slice of the vertebra, autopaving could be performed with a sufficiently small element size so that element distortion would not occur.

In the second general class of problems involving two or more implants in the same bone, the implants are in contact with each other and their orientation and position with respect to each other are fixed. In this case, the two implants can be considered as one for the purposes of application of the method. An example here would be a bone plate with multiple screws, each screw entering the bone perpendicular to the plate axis. In this case, the non-patient-specific bone-implant mesh contains material surrounding the both implants. Further, if desired, non-linear contact interface conditions between the two implants can be included in the finite element model description of the non-patient-specific bone-implant mesh. This approach could also be used when the implants were not in contact with each other but were sufficiently close to each other such that a cut plane could not be defined sufficiently far from each implant. In all cases, differently relatively-sized implants, e.g. different sized screws for a given plate size, would be analyzed by including multiple variations of the pre-constructed non-patient-specific bone-implant mesh in the library so that all possible sizes and combinations would be available.

In the third general class of problems involving two or more implants in the same bone, the implants are in contact with each other and their orientation and position with respect to each other are not fixed but depend on the surgical placement, which in turn depends in part on the patient's bone geometry and density. An example here would be a plate with a screw attached at a variable angle, or, an inter-trochanteric nail attached to a plate. One approach to this situation is to include a large number of variations of the implant-implant combinations in the library of pre-constructed non-patient-specific bone-implant meshes and then apply the method as described above, choosing a configuration from the library that matches the surgical placement. However, it may be prohibitive to pre-construct non-patient-specific bone-implant meshes for every possible set of surgical configurations applicable to all clinical situations.

In this case, the set of configurations in the library can be expanded by allowing the nodes of the pre-constructed non-patient-specific bone-implant meshes in the library to deform so that the relative positions of the two or more implants can be varied with respect to each other by very small increments. In doing so, deformations of nodes are only allowed that do not cause element distortion (to within a pre-defined measure of what constitutes a degree of element distortion that would compromise the finite element analysis). During a clinical application, each pre-constructed non-patient-specific bone-implant mesh in the library would be associated with a set of allowable nodal deformations. After specifying the position of the two or more implants, the closest matching pre-constructed non-patient-specific bone-implant finite element meshes from the library would be taken and each such pre-constructed mesh deformed within the allowable nodal deformations to find the position among the resulting models that best fits the specified configuration. Since only allowed nodal deformations could occur, this adjustment process would not result in any element distortion and thus can be fully automated and applied to any patient by an operator unskilled in the art of finite element modeling or mesh creation.

Alternatively, each pre-constructed non-patient-specific bone-implant mesh could be accompanied by a set of alternative allowable relative positions of the two or more implants, and that information could be used to choose a refined configuration for that library model that results in the best fit with the specified surgical position. The nodal coordinates of that model would then be adjusted appropriately.

This nodal adjustment method could also be used before any clinical application in order to expand the library or pre-constructed non-patient-specific bone-implant meshes.

The method may be implemented by a suitably programmed general purpose computer system, such as by machine instructions embodied in appropriate computer readable media. For example, a computer system may function as a basic computer in implementing the present invention. The computer system includes a central processing unit (CPU), such as one of the PC microprocessors or workstations or other microprocessor or microcontroller or controller, is provided and interconnected to various other components by a system bus. An operating system runs on the CPU, and provides control and is used to coordinate the function of the various components of the system. The operating system may be one of the commercially available operating systems such as Microsoft's Windows, as well as workstation, UNIX and AIX operating systems, and the like. One or more application programs, controlled by the system, are moved into and out of a main memory RAM. These programs include the program of the present invention to be subsequently described in combination with local or wide-area network systems, such as for example, the Internet. A read only memory (ROM) is connected to the CPU via the bus and includes the Basic Input/Output System (BIOS) that controls the basic computer functions. The RAM, an I/O adapter and a communications adapter are also interconnected to the system bus. The I/O adapter may be a Small Computer System Interface (SCSI) adapter that communicates with a disk storage device. The Communications adapter interconnects the bus with an outside network enabling the data processing system to communicate with other such systems over a Local Area Network (LAN) or Wide Area Network (WAN), which includes, of course, the Internet, the WEB, intranets, extranets, and other public and private networks. The terms associated with the network are meant to be generally interchangeable and are so used in the present description of the distribution network. I/O devices are also connected to the system bus via a user interface adapter and a display adapter. A keyboard and a pointing device (e.g., a mouse) are all interconnected to the bus through the user interface adapter. The display adapter includes a frame buffer, which is a storage device that holds a representation of each pixel on a monitor or a display screen. Images may be stored in the frame buffer for display on the monitor through various components, such as a digital to analog converter and the like. By using the aforementioned I/O devices, a user is capable of inputting information to the system through the keyboard (or other input device) or mouse (or other pointing system) and receiving output information from the system via display. The system also contains a memory cache and includes a portion of a disk storage drive and a portion of RAM 125.

The system, method, computer program product, and propagated signal described in this application may, of course, be embodied in hardware; e.g., within or coupled to a Central Processing Unit ("CPU"), microprocessor, microcontroller, System on Chip ("SOC"), or any other programmable device. Additionally, the system, method, computer program product, and propagated signal may be embodied in software (e.g., computer readable code, program code, instructions and/or data disposed in any form, such as source, object or machine language) disposed, for example, in a computer usable (e.g., readable) medium configured to store the software. Such software enables the function, fabrication, modeling, simulation, description and/or testing of the apparatus and processes described herein. For example, this can be accomplished through the use of general programming languages (e.g., C, C++), GDSII databases, hardware description languages (HDL) including Verilog HDL, VHDL, AHDL (Altera HDL) and so on, or other available programs, databases, nanoprocessing, and/or circuit (i.e., schematic) capture tools. Such software can be disposed in any known computer usable medium including semiconductor, magnetic disk, optical disc (e.g., CD-ROM, DVD-ROM, etc.) and as a computer data signal embodied in a computer usable (e.g., readable) transmission medium (e.g., carrier wave or any other medium including digital, optical, or analog-based medium). As such, the software can be transmitted over communication networks including the Internet and intranets. A system, method, computer program product, and propagated signal embodied in software may be included in a semiconductor intellectual property core (e.g., embodied in HDL) and transformed to hardware in the production of integrated circuits. Additionally, a system, method, computer program product, and propagated signal as described herein may be embodied as a combination of hardware and software.

One of the preferred implementations of the present invention is as a routine in an operating system made up of programming steps or instructions resident in a memory of a computing system as well known, during computer operations. Until required by the computer system, the program instructions may be stored in another readable medium, e.g. in a disk drive, or in a removable memory, such as an optical disk for use in a CD ROM computer input or in a floppy disk for use in a floppy disk drive computer input. Further, the program instructions may be stored in the memory of another computer prior to use in the system of the present invention and transmitted over a LAN or a WAN, such as the Internet, when required by the user of the present invention. One skilled in the art should appreciate that the processes controlling the present invention are capable of being distributed in the form of computer readable media in a variety of forms.

Any suitable programming language can be used to implement the routines of the present invention including C, C++, Java, assembly language, etc. Different programming techniques can be employed such as procedural or object oriented. The routines can execute on a single processing device or multiple processors. Although the steps, operations or computations may be presented in a specific order, this order may be changed in different embodiments. In some embodiments, multiple steps shown as sequential in this specification can be performed at the same time. The sequence of operations described herein can be interrupted, suspended, or otherwise controlled by another process, such as an operating system, kernel, and the like. The routines can operate in an operating system environment or as stand-alone routines occupying all, or a substantial part, of the system processing.

In the description herein, numerous specific details are provided, such as examples of components and/or methods, to provide a thorough understanding of embodiments of the present invention. One skilled in the relevant art will recognize, however, that embodiments of the invention can be practiced without one or more of the specific details, or with other apparatus, systems, assemblies, methods, components, materials, parts, and/or the like. In other instances, well-known structures, materials, or operations are not specifically shown or described in detail to avoid obscuring aspects of embodiments of the present invention.

A "computer-readable medium" for purposes of embodiments of the present invention may be any medium that can contain, store, communicate, propagate, or transport the program for use by or in connection with the instruction execution system, apparatus, system or device. The computer readable medium can be, by way of example only but not by limitation, an electronic, magnetic, optical, electromagnetic, infrared, or semiconductor system, apparatus, system, device, propagation medium, or computer memory.

A "processor" or "process" includes any human, hardware and/or software system, mechanism or component that processes data, signals or other information. A processor can include a system with a general-purpose central processing unit, multiple processing units, dedicated circuitry for achieving functionality, or other systems. Processing need not be limited to a geographic location, or have temporal limitations. For example, a processor can perform its functions in "real time," "offline," in a "batch mode," etc. Portions of processing can be performed at different times and at different locations, by different (or the same) processing systems.

Reference throughout this specification to "one embodiment", "an embodiment", or "a specific embodiment" means that a particular feature, structure, or characteristic described in connection with the embodiment is included in at least one embodiment of the present invention and not necessarily in all embodiments. Thus, respective appearances of the phrases "in one embodiment", "in an embodiment", or "in a specific embodiment" in various places throughout this specification are not necessarily referring to the same embodiment. Furthermore, the particular features, structures, or characteristics of any specific embodiment of the present invention may be combined in any suitable manner with one or more other embodiments. It is to be understood that other variations and modifications of the embodiments of the present invention described and illustrated herein are possible in light of the teachings herein and are to be considered as part of the spirit and scope of the present invention.

Embodiments of the invention may be implemented by using a programmed general purpose digital computer, by using application specific integrated circuits, programmable logic devices, field programmable gate arrays, optical, chemical, biological, quantum or nanoengineered systems, components and mechanisms may be used. In general, the functions of the present invention can be achieved by any means as is known in the art. Distributed, or networked systems, components and circuits can be used. Communication, or transfer, of data may be wired, wireless, or by any other means.

It will also be appreciated that one or more of the elements depicted in the drawings/figures can also be implemented in a more separated or integrated manner, or even removed or rendered as inoperable in certain cases, as is useful in accordance with a particular application. It is also within the spirit and scope of the present invention to implement a program or code that can be stored in a machine-readable medium to permit a computer to perform any of the methods described above.

Additionally, any signal arrows in the drawings/Figures should be considered only as exemplary, and not limiting, unless otherwise specifically noted. Furthermore, the term "or" as used herein is generally intended to mean "and/or" unless otherwise indicated. Combinations of components or steps will also be considered as being noted, where terminology is foreseen as rendering the ability to separate or combine is unclear.

As used in the description herein and throughout the claims that follow, "a", "an", and "the" includes plural references unless the context clearly dictates otherwise. Also, as used in the description herein and throughout the claims that follow, the meaning of "in" includes "in" and "on" unless the context clearly dictates otherwise.

The foregoing description of illustrated embodiments of the present invention, including what is described in the Abstract, is not intended to be exhaustive or to limit the invention to the precise forms disclosed herein. While specific embodiments of, and examples for, the invention are described herein for illustrative purposes only, various equivalent modifications are possible within the spirit and scope of the present invention, as those skilled in the relevant art will recognize and appreciate. As indicated, these modifications may be made to the present invention in light of the foregoing description of illustrated embodiments of the present invention and are to be included within the spirit and scope of the present invention.

Thus, while the present invention has been described herein with reference to particular embodiments thereof, a latitude of modification, various changes and substitutions are intended in the foregoing disclosures, and it will be appreciated that in some instances some features of embodiments of the invention will be employed without a corresponding use of other features without departing from the scope and spirit of the invention as set forth. Therefore, many modifications may be made to adapt a particular situation or material to the essential scope and spirit of the present invention. It is intended that the invention not be limited to the particular terms used in following claims and/or to the particular embodiment disclosed as the best mode contemplated for carrying out this invention, but that the invention will include any and all embodiments and equivalents falling within the scope of the appended claims. Thus, the scope of the invention is to be determined solely by the appended claims.

What is claimed as new and desired to be protected by Letters Patent of the United States is:

1. A computer-implemented method for application of finite element analysis of bone-implant systems evaluating a biomechanical performance of each bone-implant model of a set of bone-implant models for an implant implanted into a bone structure of a patient, the method comprising:
   receiving a set of patient-specific data of the bone structure;
   creating, for each bone-implant model of the set of bone-implant models, an associated patient-specific bone-implant finite element model representing at least a portion of the bone structure based on said set of patient-specific data, wherein said patient-specific bone-implant finite element model is created in part from a pre-constructed non-patient-specific bone-implant mesh; and
   determining an implant result for each particular bone-implant model of the set of bone-implant models based upon a finite element analysis of said patient-specific bone-implant finite element model associated with said particular bone-implant model.

2. The method of claim 1 wherein said patient-specific bone-implant finite element model is created in part from a pre-constructed non-patient-specific bone-implant mesh.

3. The method of claim 1 wherein said patient-specific bone-implant finite element model is created in part based on a set of pre-defined variations.

4. The method of claim 3, wherein said set of pre-defined variations includes one or more variations selected from the group consisting of an implant size variation, an implant geometry variation, an implant design variation, and combinations thereof.

5. The method of claim 3 wherein said set of pre-defined variations includes a variation in a position of the implant.

6. The method of claim 3 wherein said set of pre-defined variations includes a variation in a material property of the bone structure.

7. The method of claim 6 wherein said variation in said material property of the bone structure is based in part on a statistical atlas of said variations in said material property.

8. The method of claim 1 wherein said results are saved to a medical report.

9. The method of claim 1 further comprising: specifying an optimal implant configuration based on said implant results.

10. The method of claim 9 wherein said optimal implant configuration specifies one or more configurations selected from the group consisting of an implant size configuration, an implant geometry configuration, an implant design configuration, an implant position configuration, or any combination thereof.

11. The method of claim 1 wherein the bone structure includes at least a portion of a femur, a tibia, or a vertebra.

12. The method of claim 1 wherein the implant includes one of an implant for the hip implant, an implant for the knee, an implant for the spine, an implant for a total joint replacement, a pedicle screw, an implant for a fracture fixation, an implant for an inter-vertebral spinal fusion, a screw, a plate, a rod, or any combination thereof.

* * * * *